(12) United States Patent
Brown et al.

(10) Patent No.: US 8,293,513 B2
(45) Date of Patent: Oct. 23, 2012

(54) HISTONE DEACETYLASE INHIBITORS

(75) Inventors: Milton L. Brown, Brookeville, MD (US); Mira O. Jung, Rockville, MD (US); Anatoly Dritschilo, Bethesda, MD (US); Yali Kong, Centreville, VA (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 12/747,365

(22) PCT Filed: Dec. 12, 2008

(86) PCT No.: PCT/US2008/086603
§ 371 (c)(1),
(2), (4) Date: Jul. 30, 2010

(87) PCT Pub. No.: WO2009/079375
PCT Pub. Date: Jun. 25, 2009

(65) Prior Publication Data
US 2010/0317739 A1    Dec. 16, 2010

Related U.S. Application Data

(60) Provisional application No. 61/013,866, filed on Dec. 14, 2007.

(51) Int. Cl.
| | | |
|---|---|---|
| A61K 31/18 | (2006.01) | |
| C12N 9/99 | (2006.01) | |
| C12N 5/09 | (2010.01) | |
| A61P 35/00 | (2006.01) | |
| C07C 303/00 | (2006.01) | |
| C07C 307/00 | (2006.01) | |
| C07C 309/00 | (2006.01) | |
| C07C 311/00 | (2006.01) | |

(52) U.S. Cl. ........... 435/184; 435/375; 514/603; 564/86
(58) Field of Classification Search ........... 564/86; 514/603; 435/184, 375
See application file for complete search history.

(56) References Cited

U.S. PATENT DOCUMENTS

| | | | |
|---|---|---|---|
| 5,387,681 A | 2/1995 | Miller et al. | |
| 6,140,505 A | 10/2000 | Kunda et al. | |
| 2002/0143037 A1 | 10/2002 | Lan-Hargest et al. | |
| 2002/0143052 A1 | 10/2002 | Lan-Hargest et al. | |
| 2002/0143196 A1 | 10/2002 | Lan-Hargest et al. | |
| 2003/0083521 A1 | 5/2003 | Lan-Hargest et al. | |
| 2003/0125306 A1 | 7/2003 | Lan-Hargest et al. | |
| 2003/0129724 A1 | 7/2003 | Grozinger et al. | |
| 2003/0162293 A1 | 8/2003 | Chu et al. | |
| 2003/0216345 A1 | 11/2003 | Nakanishi et al. | |
| 2003/0224473 A1 | 12/2003 | McCafferty | |
| 2004/0002506 A1 | 1/2004 | Breslow et al. | |
| 2004/0023944 A1 | 2/2004 | Lan-Hargest et al. | |
| 2004/0029903 A1 | 2/2004 | Lan-Hargest et al. | |
| 2004/0029922 A1 | 2/2004 | Lan-Hargest et al. | |
| 2004/0077698 A1 | 4/2004 | Georges et al. | |
| 2004/0077726 A1 | 4/2004 | Watkins et al. | |
| 2004/0087652 A1 | 5/2004 | Goettlicher et al. | |
| 2004/0092598 A1 | 5/2004 | Watkins et al. | |
| 2004/0198830 A1 | 10/2004 | Watkins et al. | |
| 2004/0224991 A1 | 11/2004 | Lu et al. | |
| 2004/0229889 A1 | 11/2004 | Urano et al. | |
| 2004/0254220 A1 | 12/2004 | Bressi et al. | |
| 2004/0266769 A1 | 12/2004 | Bressi et al. | |
| 2005/0014839 A1 | 1/2005 | Kozikowski et al. | |
| 2005/0032831 A1 | 2/2005 | Kozikowski et al. | |
| 2005/0085515 A1 | 4/2005 | Watkins et al. | |
| 2005/0107348 A1 | 5/2005 | Lan-Hargest et al. | |
| 2005/0107445 A1 | 5/2005 | Watkins et al. | |
| 2005/0124679 A1 | 6/2005 | Kim et al. | |
| 2005/0137232 A1 | 6/2005 | Bressi et al. | |
| 2005/0137234 A1 | 6/2005 | Bressi et al. | |
| 2005/0143385 A1 | 6/2005 | Watkins et al. | |
| 2005/0159470 A1 | 7/2005 | Bressi et al. | |
| 2005/0171103 A1 | 8/2005 | Stokes et al. | |
| 2005/0171208 A1 | 8/2005 | Lan-Hargest et al. | |
| 2005/0176686 A1 | 8/2005 | Maurer et al. | |
| 2005/0234033 A1 | 10/2005 | Anandan et al. | |
| 2005/0277583 A1 | 12/2005 | Yoshida et al. | |
| 2005/0282890 A1 | 12/2005 | Lan-Hargest et al. | |
| 2006/0018921 A1 | 1/2006 | Levenson et al. | |
| 2006/0047123 A1 | 3/2006 | Ahmed et al. | |
| 2006/0052599 A1 | 3/2006 | Ishibashi et al. | |
| 2006/0058282 A1 | 3/2006 | Finn et al. | |
| 2006/0079528 A1 | 4/2006 | Finn et al. | |
| 2006/0106049 A1 | 5/2006 | Odenike | |
| 2006/0122234 A1 | 6/2006 | Archer et al. | |
| 2006/0160902 A1 | 7/2006 | Wiech et al. | |

(Continued)

FOREIGN PATENT DOCUMENTS

WO        WO97/18194        5/1997

(Continued)

OTHER PUBLICATIONS

Ljunggren et al. Fibrin-stabilizing factor inhibitors. 11. Monodansylated Weak Aliphatic Diamine. Journal of Medicinal Chemistry, 1974, vol. 17, No. 6.*
Acharya et al., "Rational Development of Histone Deacetylase Inhibitors as Anticancer Agents: A Review," Molecular Pharmacology, 68(4):917-932 (2005).
Bouchain et al., "Development of Potential Antitumor Agents. Synthesis and Biological Evaluation of a New Set of Sulfonamide Derivatives as Histone Deacetylase Inhibitors," J. Med. Chem., 46(5):820-830 (2003).
Bouchain et al., "Novel hydroxamate and anilide derivatives as potent histone deacetylase inhibitors: synthesis and antiproliferative evaluation," Curr Med Chem 10(22):2359-2372 (2003).
Chen et al., "Chemistry and biology of mercaptoacetamides as novel histone deacetylase inhibitors," Bioorg Med Chem Lett 15:1389-1392 (2005).
Curtin, M., "Current patent status of histone deacetylase inhibitors," Expert Opin. Ther. Patents, 12(9):1375-1384 (2002).

(Continued)

Primary Examiner — Brandon Fetterolf
Assistant Examiner — Anna Pagonakis
(74) Attorney, Agent, or Firm — McKeon, Meunier, Carlin & Curfman, LLC

(57) ABSTRACT

Novel histone deacetylase inhibitors, including novel fluorescent histone deacetylase inhibitors, are described. Methods for making and using the same, e.g., to treat cancer, are provided.

21 Claims, 6 Drawing Sheets

U.S. PATENT DOCUMENTS

| | | | |
|---|---|---|---|
| 2006/0205941 | A1 | 9/2006 | Bressi et al. |
| 2006/0235231 | A1 | 10/2006 | Joel et al. |
| 2006/0241129 | A1 | 10/2006 | Breslow et al. |
| 2006/0258694 | A1 | 11/2006 | Bressi et al. |
| 2007/0004806 | A1 | 1/2007 | Kalvinsh et al. |
| 2007/0010536 | A1 | 1/2007 | Breslow et al. |
| 2007/0010669 | A1 | 1/2007 | Breslow et al. |
| 2007/0015809 | A1 | 1/2007 | Bressi et al. |
| 2007/0037869 | A1 | 2/2007 | Lan-Hargest et al. |
| 2007/0088043 | A1 | 4/2007 | Srinivas et al. |
| 2007/0098816 | A1 | 5/2007 | Nakanishi et al. |
| 2007/0149495 | A1 | 6/2007 | Bressi et al. |
| 2007/0173527 | A1 | 7/2007 | Bressi et al. |
| 2007/0185071 | A1 | 8/2007 | Yoshida et al. |
| 2007/0219244 | A1 | 9/2007 | Jenssen et al. |
| 2007/0232696 | A1 | 10/2007 | Gottlicher et al. |

FOREIGN PATENT DOCUMENTS

| | | | |
|---|---|---|---|
| WO | 0118171 | A2 | 3/2001 |
| WO | WO01/18171 | | 3/2001 |
| WO | 0138322 | A1 | 5/2001 |
| WO | 0170675 | A2 | 9/2001 |
| WO | WO02/30879 | | 4/2002 |
| WO | 03070691 | A1 | 8/2003 |
| WO | WO03/082288 | | 10/2003 |
| WO | WO2005/011661 | | 2/2005 |
| WO | 2005092844 | A1 | 10/2005 |
| WO | WO2005/108367 | | 11/2005 |
| WO | WO2006/017214 | | 2/2006 |
| WO | WO2006/017215 | | 2/2006 |
| WO | WO2006/123121 | | 11/2006 |

OTHER PUBLICATIONS

Duvic et al., "Phase 2 trial of oral vorinostat (suberoylanilide hydroxannic acid, SAHA) for refractory cutaneous T-cell lymphoma (CTCL)," Blood, 109(1):31 (2007).

Finn et al., "Novel Sufonamide Derivatives as Inhibitors of Histone Deacetylase," Helvetica Chimica Acta, 88 (7):1630-1657 (2005).

Flatmark et al., "Radiosensitization of colorectal carcinoma cell lines by histone deacetylase inhibition," Radiation Oncology, 1:25 (2006).

Fournel et al., "Sulfonamide Anilides, a Novel Class of Histone Deacetylase Inhibitors, Are Antiproliferative against Human Tumors," Cancer Research, 62:4325-4330 (2002).

Fuino et al., "Histone deacetylase inhibitor LAQ824 down-regulates Her-2 and sensitizes human breast cancer cells to trastuzumab, taxotere, gemcitabine, and epothilone B," Molecular Cancer Therapeutics, 2:971-984 (2003).

Hilgetag et al., Preparative Organic Chemistry, J. Wiley and Sons, 1972, p. 670.

Johnson, T., "The Synthesis of Sulfonyl Chlorides by Chlorination of Sulphur Compounds," Proc. Natl. Acad. Sci. USA, 25(9):448-452 (1939).

Karagiannis et al., "Clinical Potential of Histone Deacetylase Inhibitors as Stand Alone Therapeutics and in Combination with Other Chemotherapeutics or Radiotherapy for Cancer," Epigenetics, 1(3):121-126 (2006).

Kelly et al., "Phase I Clinical Trial of Histone Deacetylase Inhibitor: Suberoylanilide Hydroxamic Acid Adminstered Intravenously," Clinical Cancer Research, 9:3578-3588 (2003).

Keshelava et al., "Histone Deacetylase 1 Gene Expression and Sensitization of Multidrug-Resistant Neuroblastoma Cell Lines to Cytotoxic Agents by Depsipeptide," J Natl Cancer Inst 99:1107-1119 (2007).

Kim et al., "Histone Deacetylase Inhibitor—Mediated Radiosensitization of Human Cancer Cells: Class Differences and the Potential Influence of p53," Clin Cancer Res, 12(3):940-949 (2006).

Kim et al., "Oxamflatin is a novel antitumor compound that inhibits mammalian histone deacetylase," Oncogene, 18:2461-2470 (1999).

Konsoula et al., "In vitro plasma stability, permeability and solubility of mercaptoacetamide histone deacetylase inhibitors," Int J Pharm 361:19-25 (2008).

Konsoula et al., "Involvement of p-glycoprotein and multidrug resistance associated protein 1 on the transepithelial transport of a mercaptoacetamide-based histone-deacetylase inhibitor in caco-2 cells," Bio Pharm Bull 32:74-78 (2009).

Konsoula et al., "Pharmacokinetics-pharmacodynamics and antitumor activity of mercaptoacetamide-based histone deacetylase inhibitors," Mol Cancer Ther 8:2844-2851 (2009).

Lavoie et al., "Design and synthesis of a novel class of histone deacetylase inhibitors," Bioorg Med Chem Lett, 11 (21):2847-2850 (2001).

Marks et al., "Histone deacetylase inhibitors: discovery and development as anticancer agents," Expert Opin. Investig. Drugs 14(12):1497-1511 (2005).

Marson et al., "Stereodefined and Polyunsaturated Inhibitors of Histone Deacetylasebased on (2E,4E)-5-Arylpenta-2,4-dienoic Acid Hydroxyamides," Bioorg. Med. Chem. Lett., 14:2477-2481 (2004).

Matter et al., "Affinity and Selectivity of Matrix Metalloproteinase Inhibitors: A Chemometrical Study from the Perspective of Ligands and Proteins," Journal of Medicinal Chemistry, 42(22): 4506-4523 (1999).

Matter et al., "Quantitative Structure-Activity Relationship of Human Neutrophil Collagenase (MMP-8) Inhibitors Using Comparative Molecular Field Analysis and X-ray Structure Analysis," Journal of Medicinal Chemistry, 42(11):1908-1920 (1999).

Miller, T., "Patent status of histone deacetylase inhibitors," Expert Opin Ther Patents, 14(6):791-804 (2004).

Minucci et al., "Histone deacetylase inhibitors and the promise of epigenetic (and more) treatments for cancer," Nature Cancer Research, 6:38-51 (2006).

Moradei et al., "Histone Deacetylase Inhibitors: Latest Developments, Trends and Prospects," Curr Med Chem—Anti-Cancer Agents, 5:529-560 (2005).

Morissette et al., "High-throughput crystallization: polymorphs, salts, co-crystals and solvates of pharmaceutical solids," Advanced Drug Delivery Reviews, 56:275-300 (2004).

Munshi et al., "Histone Deacetylase Inhibitors Radisensitize Human Melanoma Cells by Suppressing DNA Repair Activity," Clin Cancer Res 11(13):4912-4922 (2005).

Novotny-Diermayr et al., "SB939, a novel potent and orally active histone deacetylase inhibitor with high tumor exposure and efficacy in mouse models of colorectal cancer," Molecular Cancer Therapy 9:642-651 (2010).

Plumb et al., "Pharmacodynamic Response and Inhibition of Growth of Human Tumor Xenografts by the Novel Histone Deacetylase Inhibitor PXD101," Molecular Cancer Therapeutics, 2:721-728 (2003).

Price et al., "Histone deacetylase inhibitors: an analysis of recent patenting activity," Expert Opin. Ther. Patents 17 (7):745-765 (2007).

Richon et al., "Histone Deacetylase Inhibitors: A New Class of Potential Therapeutic Agents for Cancer Treatment," Clinical Cancer Research, 8:662-664 (2002).

Sandor et al., "Phase I Trial of the Histone Deacetylase Inhibitor, Depsipeptide (FR901228, NSC 630176), in Patients with Refractory Neoplasms," 8:718-728 (2002).

Spencer et al., "Role of covalent modifications of histones in regulating gene expression," Gene, 240(1):1-12 (1999).

Subramanian et al., "Ku70 acetylation mediates neuroblastoma cell death induced by histone deacetylase inhibitors," PNAS 102(13):4842-4847 (2005).

Thomas et al., "Synthesis and biological evaluation of the suberoylanilide hydroxamic acid (SAHA) β-glucuronide and β-galactoside for application in selective prodrug chemotherapy," 17(4):983-986 (2007).

Unknown, "Small molecule inhibitors of histone deacetylase," Expert Opin. Ther. Patents, 12(6): 943-947 (2002).

Weinmann et al., "Histone deacetylase inhibitors: a survey of recent patents," Expert Opin Ther Patents, 15 (12):1677-1690 (2005).

Zhang et al., "Enhancement of radiation sensitivity of human squamous carcinoma cells by histone deacetylase inhibitors," Radiation Research, 161(6):667-674 (2004).

Extended European Search Report, dated May 8, 2012, in corresponding European Application No. 08862332.7, 13 pages.

* cited by examiner

HISTONE DEACETYLASE INHIBITORS

CROSS-REFERENCE TO RELATED APPLICATIONS

This application claims the benefit of U.S. Provisional Application 61/013,866, filed Dec. 14, 2007, the entire disclosure of which is hereby incorporated by reference in its entirety.

STATEMENT AS TO FEDERALLY SPONSORED RESEARCH

Certain aspects of the disclosure provided herein were funded, in whole or in part, by the National Institute of Health P01 Grant # CA07417501. The Government has certain rights in the invention.

TECHNICAL FIELD

This disclosure relates to histone deacetylase inhibitors (HDAC inhibitors), including, in particular, fluorescent histone deacetylase inhibitors, compositions including the same, and methods for preparing and using the same.

BACKGROUND

Cancers are among the most common causes of death in developed countries. Despite continuing advances, the existing treatments exhibit undesirable side effects and limited efficacy. Identifying new effective cancer drugs is a continuing focus of medical research.

DNA in eukaryotic cells is tightly complexed with proteins (histones) to form chromatin. Histones are small, positively charged proteins that are rich in basic amino acids, which contact the negatively charged phosphate groups of DNA. There are five main classes of histones: H1, H2A, H2B, H3, and H4. Histones are synthesized during the S phase of the cell cycle, and newly synthesized histones enter the nucleus to become associated with DNA.

The amino acid side chains of histones may be modified by post-translational addition of methyl, acetyl, or phosphate groups, neutralizing the positive charge of the side chain, or converting it to a negative charge. For example, lysine and arginine groups may be methylated, lysine groups may be acetylated, and serine groups may be phosphorylated. Methylation, acetylation, and phosphorylation of amino termini of histones that extend from the nucleosomal core affect chromatin structure and gene expression. Spencer, et al., *Gene*, 1999, 240, 11-12.

Acetylation and deacetylation of histones is associated with transcriptional events leading to cell proliferation and/or differentiation. Regulation of the function of transcriptional factors is also mediated through acetylation. The acetylation status of histones is correlated with the transcription of genes. Histone acetylases (e.g., histone acetyltransferases (HAT)) and deacetylases (histone deacetylases or HDACs), which regulate the acetylation state of histones have been identified in many organisms and have been implicated in the regulation of numerous genes. In general, histone acetylation is associated with transcriptional activation, whereas histone deacetylation is associated with gene repression. Histone deacetylases (HDACs) repress gene transcription by modulating histone acetylation. Some non-histone proteins, many of which are transcription factors, are also substrates of HDACs.

A growing number of histone deacetylase isoforms have been identified. The histone deacetylase family is subdivided into three categories based on sequence similarity to the yeast proteins RPD3 (class I: HDAC1, 2, 3, and 8), HDA1 (class II: HDAC4, 5, 6, 7, 9, and 10), and SIR2 (class III), while HDAC11 (class IV) shares some similarity to class I and class II, and can be considered to lie at the boundary between the two classes. The class I HDACs includes HDAC1, HDAC2, HDAC3, and HDAC8, which exhibit high sequence identity and similar domain organization, and are similar to the yeast RPD3 protein factor involved in gene transcription regulation. Class II HDACs, HDAC4, HDAC5, HDAC6, HDAC7, HDAC9, and HDAC10, are similar to yeast histone deacetylase, a complex with the active part carried by the HDA1 catalytic subunit. A third class of deacetylases (class III) (sirtuins 1-7) includes the SIR2 (silent information regulator)-like family of NAD-dependent deacetylases.

Although HDACs are involved in many cellular functions, such as cell cycling and apoptosis, the best-characterized function of Class I and II HDACs is transcriptional repression. Histone deacetylases function as part of large multiprotein complexes, which are tethered to the promoter and repress transcription. Transcriptional repression is directly associated with the recruitment of multiprotein complexes containing histone deacetylases. Well characterized transcriptional repressors such as MAD, nuclear receptors and YY1 associate with histone deacetylase complexes to exert their repressor function. Histone deacetylases have been found in association with multiprotein complexes, with some distinctions between class I and class II deacetylases. For example, class I but not class II histone deacetylases are found in association with a mouse protein mSin3a which is known to bind to MAD (a Sin3/HDAC complex), and in association with multiprotein complexes known as NuRD/Mi2/NRD. On the other hand, class II HDACs are involved in shuttling between the nucleus and the cytoplasm. However, both class I and class II HDACs possess well-conserved deacetylase core domains of approximately 400 amino acids and apparently identical zinc-dependent catalytic machinery. Class III HDACs require nicotinamide-adenine dinucleotide as a cofactor, and, at least in yeast, sense the metabolic state and age of the cell. A mammalian homolog of SIR2, SirT1, deacetylates p53, altering its function as an apoptotic protein, and another, SirT2, is a microtubule deacetylase.

Aberrant histone deacetylase activity and/or levels are believed to be associated with a variety of different disease states including, but not limited to cell proliferative diseases and conditions such as leukemia, melanomas/squamous cell carcinomas, breast cancer, prostate cancer, bladder cancer; lung cancer, ovarian cancer and colon cancer. Histone deacetylase inhibitors exhibit various beneficial anticancer effects on cancer cells, including inducing cellular differentiation, up-regulating tumor suppressor gene expression, reducing tumor growth, inducing apoptotic cell death, and inhibiting angiogenesis. In addition to their direct effects, histone deacetylase inhibitors also enhance the beneficial effects of other agents by sensitizing cancer cells to the effect of other chemotherapeutic agents or the effects of radiation.

As a result of these beneficial effects, the development of novel histone deacetylase inhibitors as potential novel anticancer agents has been a topic of considerable research interest. For example, hydroxamic acid-containing inhibitors have been made which are high affinity reversible inhibitors of both class I and II HDACs. Trichostatin A (TSA) ((R,2E,4E)-7-(4-(dimethylamino)phenyl)-N-hydroxy-4,6-dimethyl-7-oxohepta-2,4-dienamide) was one of the first histone deacetylase inhibitors to be described and is widely used as a reference in research. The recently approved cancer drug suberoylanilide hydroxamic acid (SAHA) is also of this class, which also includes sulfonamides such as oxamflatin ((E)-N-hydroxy-5-(3-(phenylsulfonamido)phenyl)pent-2-en-4-ynamide), a compound with demonstrated anti-tumor activity, and belinostat (PXD101) ((E)-N-hydroxy-3-(4-(N-phenylsulfamoyl)phenyl)acrylamide), which inhibited growth of human cisplatin-resistant ovarian tumor xenografts of cells. Other hydroxamic-acid-sulfonamide inhibitors of histone deacetylase are described in: Lavoie, et al., *Bioorg. Med. Chem. Lett.*, 2001, 11, 2847-50; Bouchain, et al., *J. Med. Chem.*, 2003, 846, 820-830; Bouchain, et al., *Curr. Med. Chem.*, 2003, 10, 2359-2372; Marson, et al., *Bioorg. Med. Chem. Lett.*, 2004, 14, 2477-2481; Finn, et al., *Helv. Chim. Acta*, 2005, 88, 1630-1657; WO2002030879; WO2003082288; WO20050011661; WO2005108367; WO2006123121; WO2006017214; WO2006017215; US2005/0234033. Other structural classes of histone deacetylase inhibitors include short chain fatty acids, cyclic peptides, and benzamides. Acharya, et al., *Mol. Pharmacol.*, 2005, 68, 917-932.

SUMMARY

In spite of the advances set forth above, the need continues to exist for new and more effective inhibitors of histone deacetylases. Of particular interest is the development of compounds that may inhibit the various isoforms of histone deacetylases selectively. Another need is the development of new compounds that enable probing of the mechanism of histone deacetylase inhibitor activity, e.g., such as by the use of fluorescent histone deacetylase inhibitors.

This disclosure is directed to compounds that function as histone deacetylase inhibitors, and thus find therapeutic utility in the treatment of a variety of diseases or disorders. The compositions and methods can be used to treat, for example, diseases or disorders associated with aberrant histone deacetylase activity or levels, including, for example, cancer.

The disclosure is also directed to the finding that certain of the histone deacetylase inhibitors described herein are fluorescent, and can be used as theragnostic agents to detect and/or treat a variety of disorders associated with aberrant (e.g., increased) histone deacetylase activity or levels. For example, in some cases, a fluorescent histone deacetylase inhibitor can be used as a diagnostic agent (e.g., to diagnose diseases or conditions in which aberrant levels or activity of histone deacetylase are associated); as a combined diagnostic/therapeutic agent (e.g., to indicate the presence of one or more cells exhibiting aberrant histone deacetylase activity and/or levels and to treat such cells); and as a tracking/therapeutic agent (e.g., to determine the location of the fluorescent inhibitor in order to help direct and/or potentiate an additional therapy such as surgery or radiation).

The histone deacetylase inhibitors described herein, whether fluorescent or not, can exhibit a broad range of histone deacetylase inhibition, e.g., can inhibit both class I and class II HDACs in a pan-HDAC assay, and/or can exhibit selectivity towards a certain class of HDACs (e.g., class II) or one or more histone deacetylase isozymes (e.g., HDAC6).

Certain of the histone deacetylase inhibitors described herein may operate by a novel mechanism whereby they localize in the cytoplasm yet nonetheless inhibit nuclear histone deacetylation. For example, fluorescent histone deacetylase inhibitors described herein localize in the cytoplasm but not the nucleus, as evidenced by fluorescence localization assays, yet exhibit inhibitory effects on the deacetylation of nuclear histones, as evidenced by increased acetylation of nuclear histones. Thus, the inhibitors described herein may inhibit the HDACs that are shuttling between the cytoplasm and the nucleus, but do not localize (and are not transported) to the nucleus themselves. Accordingly, the histone deacetylase inhibitors described herein eliminate the need for a mechanism for nuclear localization of the inhibitor. In addition, the inhibitors also cause the relative concentration of HDACs in the cytoplasm as compared to the nucleus to be increased. Moreover, acetylation of cytoplasmic tubulin is increased with use of the histone deacetylase inhibitors described herein, further demonstrating the cytoplasmic localization of the histone deacetylase inhibitors, and suggesting another mechanism (tubulin deacetylation inhibition) by which histone deacetylase inhibition results in beneficial anticancer effects.

Accordingly, in one aspect, provided herein is a compound according to formula I:

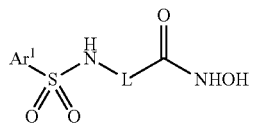

or a salt thereof;
wherein:
-L- is a divalent aliphatic hydrocarbon or oxygenated hydrocarbon linking group comprising a chain of 4, 5, 6, 7, or 8 atoms as the shortest chain of atoms separating its attachment points, wherein the atoms forming the bonds to the remainder of the molecule are carbon atoms;

$Ar^1$ is selected from the group consisting of unsubstituted or substituted naphthyl and unsubstituted or substituted fused bicyclic heteroaryl, wherein the substituents of the naphthyl or bicyclic heteroaryl are selected from the group consisting of —$R^1$; —$Ar^2$; —($C_1$-$C_3$)alkylene-$Ar^2$; ($C_2$-$C_6$)alkenyl; ($C_2$-$C_6$)alkynyl; halogen; —C≡N; —$NO_2$; —C(=O)$R^3$; —C(=O)O$R^3$; —C(=O)N$R^4_2$; —C(=N$R^3$)N$R^4_2$; —O$R^2$; —OC(=O)($C_1$-$C_6$)alkyl; —OC(=O)($C_1$-$C_6$)alkylene-$R^5$; —OC(=O)O($C_1$-$C_6$)alkyl; —OC(=O)N$R^4_2$; —N$R^4_2$; —N$R^4$C(=O)$R^3$; —N$R^4$C(=O)$Ar^2$; —N$R^4$C(=O)O($C_1$-$C_6$)alkyl; —N$R^4$C(=O)N$R^4_2$; —N$R^4$S$O_2R^3$; —N$R^4$S$O_2Ar^2$; —S$R^2$; —S(O)$R^2$; —S$O_2R^2$; —OS$O_2$($C_1$-$C_6$)alkyl; —OS$O_2Ar^2$; and —S$O_2$N$R^4_2$;

each $R^1$ is independently unsubstituted ($C_1$-$C_6$)alkyl or ($C_1$-$C_6$)alkyl substituted with up to five halogen atoms and up to two substituents selected from the group consisting of —C(=O)O$R^3$; —C(=O)N$R^4_2$; —O$R^3$; —OC(=O)($C_1$-$C_6$)alkyl; —OC(=O)O($C_1$-$C_6$)alkyl; —OC(=O)N$R^4_2$; —N$R^4_2$; —N$R^3$C(=O)$R^3$; —N$R^3$C(=O)N$R^4_2$; —S($C_1$-$C_6$)alkyl; —S(O)($C_1$-$C_6$)alkyl; and —S$O_2$($C_1$-$C_6$)alkyl;

each $R^2$ is independently selected from the group consisting of hydrogen, $R^1$, $Ar^2$ and ($C_1$-$C_3$)alkylene-$Ar^2$;

each $R^3$ is independently hydrogen or ($C_1$-$C_6$)alkyl;

each $R^4$ is independently hydrogen; ($C_1$-$C_6$)alkyl; —($C_2$-$C_6$)alkylene-O$R^3$; —($C_1$-$C_6$)alkylene-C(=O)O$R^3$; —($C_1$-$C_6$)alkylene-OC(=O)$R^3$; —($C_2$-$C_6$)alkylene-N$R^6_2$; —($C_1$-$C_6$)alkylene-C(=O)N$R^6_2$; —($C_1$-$C_6$)alkylene-N$R^3$C(=O)$R^3$; —($C_1$-$C_6$)alkylene-N$R^3$C(=O)N$R^6_2$; $Ar^2$, or —($C_1$-$C_3$)-alkylene$Ar^2$; or, optionally, within any occurrence of N$R^4_2$, independently of any other occurrence of N$R^4_2$, the two $R^4$ groups in combination are —$(CH_2)_a$— or —$(CH_2)_b$A$(CH_2)_2$—;

each $R^5$ is independently $Ar^2$ or 1,4-benzoquinon-2-yl optionally substituted with 0, 1, 2, or 3 alkyl groups;

each $R^6$ is independently hydrogen; ($C_1$-$C_6$)alkyl; —($C_2$-$C_6$)alkylene-O$R^3$; —($C_1$-$C_6$)alkylene-C(=O)O$R^3$; —($C_1$-

$C_6$)alkylene-OC(=O)$R^3$; ($C_2$-$C_6$)alkylene-N$R^3{}_2$; —($C_1$-$C_6$)alkylene-C(=O)N$R^3{}_2$; —($C_1$-$C_6$)alkylene-N$R^3$C(=O)$R^3$; —($C_1$-$C_6$)alkyleneN$R^3$C(=O)N$R^3{}_2$; —$Ar^2$, or —($C_1$-$C_3$)alkylene-$Ar^2$; or, optionally, within any occurrence of N$R^6{}_2$, independently of any other occurrence of N$R^6{}_2$, the two $R^6$ groups in combination are —(CH$_2$)$_a$— or —(CH$_2$)$_b$A(CH$_2$)$_2$—;

each a is independently selected from the group consisting of 4, 5, and 6;

each b is independently selected from the group consisting of 2 and 3;

each A is independently selected from the group consisting of O, S, N$R^3$; NC(=O)$R^3$; NSO$_2R^3$; N($C_2$-$C_6$)alkylene-O$R^3$; N($C_1$-$C_6$)alkylene-C(=O)O$R^3$; N($C_1$-$C_6$)alkylene-OC(=O)$R^3$; N($C_2$-$C_6$)alkylene-N$R^3{}_2$; N($C_1$-$C_6$)alkylene-C(=O)N$R^3{}_2$; N($C_1$-$C_6$)alkylene-N$R^3$C(=O)$R^3$; N($C_1$-$C_6$)alkylene-N$R^3$C(=O)N$R^3{}_2$; N$Ar^2$; N($C_1$-$C_3$)alkylene-$Ar^2$; and NC(=O)$Ar^2$;

each $Ar^2$ is independently selected from the group consisting of unsubstituted aryl, unsubstituted heteroaryl, and aryl or heteroaryl substituted with one or more substituents independently selected from the group consisting of ($C_1$-$C_6$)alkyl; ($C_2$-$C_6$)alkenyl; ($C_2$-$C_6$)alkynyl; halogen; —C≡N; —NO$_2$; —C(=O)$R^3$; —C(=O)O$R^3$; —C(=O)N$R^3{}_2$; —C(=N$R^3$)N$R^3{}_2$; —O$R^3$; —OC(=O)($C_1$-$C_6$)alkyl; —OC(=O)O($C_1$-$C_6$)alkyl; —OC(=O)N$R^3{}_2$; —N$R^3{}_2$; —N$R^3$C(=O)$R^3$; —N$R^3$C(=O)O($C_1$-$C_6$)alkyl; —N$R^3$C(=O)N$R^3{}_2$; —S($C_1$-$C_6$)alkyl; —S(O)($C_1$-$C_6$)alkyl; and —SO$_2$($C_1$-$C_6$)alkyl; —SO$_2$N$R^3{}_2$; and ($C_1$-$C_3$)perfluoroalkyl.

In another aspect, a pharmaceutical composition comprising a pharmaceutically acceptable carrier and a compound according to formula I, or a pharmaceutically acceptable salt thereof, is provided.

There are also provided therapeutic methods of using the compounds according to formula I, or pharmaceutical compositions comprising the same. A method can include causing a compound of formula I to be present in an individual, such as by administering a compound of formula I or a pharmaceutically acceptable salt thereof, to an individual, or administering a prodrug of the same to an individual. A therapeutic method can be, e.g., a method to treat a disease or disorder associated with aberrant histone deacetylase activity and/or level, such as cancer.

A method of inhibiting a histone deacetylase is also provided, which comprises contacting an effective amount of compound according to formula I, or a salt thereof, with a histone deacetylase. In particular embodiments, the histone deacetylase can be selected from HDAC1, HDAC2, HDAC3, HDAC6, and HDAC8. In other embodiments, the histone deacetylase is a class I deacetylase, or a class II deacetylase. In yet other embodiments, a plurality of HDACs is contacted, e.g., a pan-HDAC assay.

In another aspect, there is provided a method of increasing the amount of histone acetylation in a cell comprising contacting the cell with an effective amount of compound according to formula I, or a salt thereof.

Also provided are methods of increasing the amount of tubulin acetylation and/or inhibiting tubulin deacetylation in a cell comprising contacting the cell with an effective amount of compound according to formula I, or a salt thereof.

In another aspect, there is provided a method of treating a histone deacetylase-associated disease or condition comprising causing an effective amount of a compound according to formula I, or a salt thereof, to be present in an individual in need of such treatment. Causing an effective amount of a compound according to formula I, or a salt thereof, to be present in an individual can occur, e.g., by administering a compound of formula I or a pharmaceutically acceptable salt thereof, to an individual, or administering a prodrug of the same to an individual.

Further provided is a method of inducing cell-cycle arrest and/or apoptosis of a cell comprising contacting a cell with a compound according to formula I, or a salt thereof.

Also described is a method for treating cancer comprising causing an effective amount of a compound according to formula I, or a salt thereof, to be present in an individual in need of such treatment.

In another aspect, there is provided a method of killing a tumor cell comprising contacting the tumor cell with an effective amount of a compound according to formula I, or a salt thereof, and irradiating the tumor cell with an effective amount of ionizing radiation.

Further, there is provided a method of killing a tumor cell comprising contacting the tumor cell with an effective amount of a compound according to formula I, or a salt thereof, and contacting the tumor cell with an effective amount of at least one further chemotherapeutic agent.

There is also provided a method of treating a tumor in an individual comprising causing an effective amount of a compound according to formula I, or a salt thereof, to be present in the individual; and irradiating the tumor with an effective amount of ionizing radiation.

There is also provided a method of trapping histone deacetylase in the cytoplasm of a cell comprising contacting the cell with an effective amount of a compound according to formula I, or a salt thereof; whereby the contacting results in an increase in the relative concentration of histone deacetylase in the cytoplasm of the cell as compared to the nucleus of the cell.

There is also provided a method of detecting histone deacetylase inhibitory activity of a compound comprising contacting the compound with a cell; comparing the distribution of a histone deacetylase in the cell after contacting with the distribution of the histone deacetylase in the cell before contacting or the distribution of the histone deacetylase in a control cell which has not been contacted with the compound to determine whether the contacting with the compound results in an increase in the relative concentration of histone deacetylase in the cytoplasm of the cell as compared to the nucleus of the cell; and identifying a compound, the contacting of which results in an increase in the relative concentration of histone deacetylase in the cytoplasm of the cell as compared to the nucleus of the cell, as an inhibitor of histone deacetylase.

In other aspects, methods of using fluorescent histone deacetylase inhibitors are provided. The methods take advantage of the fluorescent properties of the molecules to enable diagnostic and/or therapeutic applications, or to enable guided treatments (e.g., radiotherapy or surgery). In particular, there is provided a method of detecting the presence of an elevated amount of a histone deacetylase in a subject cell comprising providing a fluorescent histone deacetylase inhibitor; contacting the fluorescent histone deacetylase inhibitor with the subject cell and with a control cell; and observing fluorescence of the subject cell and control cell after the contacting; wherein an elevated level of fluorescence of the subject cell relative to the level of fluorescence of the control cell is indicative of an elevated amount of histone deacetylase in the subject cell as compared to the control cell.

As another method of using fluorescent histone deacetylase inhibitors, there is provided a method of detecting diseased (e.g., cancerous) cells in a tissue, comprising providing a fluorescent histone deacetylase inhibitor; contacting the fluorescent histone deacetylase inhibitor with tissue of an individual; and observing for fluorescence of at least some of the cells of the tissue after the contacting; wherein an elevated level of fluorescence of at least some of the cells relative to others in the tissue or relative to control non-diseased cells that have been contacted with the fluorescent histone deacetylase inhibitor is indicative that the fluorescent cells may be diseased cells comprising elevated amounts of histone deacetylase. In some embodiments, the fluorescent histone deacetylase inhibitor is a fluorescent histone deacetylase inhibitor according to formula I, or a salt thereof.

Also provided is a method of radiotherapy of a tumor comprising providing a fluorescent histone deacetylase inhibitor; causing the fluorescent histone deacetylase inhibitor to be present in at least some tumor cells in an effective amount to inhibit a histone deacetylase and for fluorescence to be observable; observing the fluorescence; and directing an effective amount of ionizing radiation to the fluorescent tumor cells. In some embodiments, the fluorescent histone deacetylase inhibitor is a fluorescent histone deacetylase inhibitor according to formula I, or a salt thereof.

In yet another aspect, there is provided a method of guided surgery to remove at least a portion of a tumor from an individual, comprising providing a fluorescent histone deacetylase inhibitor; causing the fluorescent histone deacetylase inhibitor to be present in at least some cells of the tumor tissue in an effective amount for fluorescence of a portion of the tumor tissue to be observable; observing the fluorescence; and surgically removing at least some of the fluorescent tumor tissue, whereby at least a portion of the tumor that comprises fluorescent tumor cells is removed. In some embodiments, the fluorescent histone deacetylase inhibitor is a fluorescent histone deacetylase inhibitor according to formula I, or a salt thereof.

In another aspect, a method for predicting the susceptibility of a cancer to treatment with histone deacetylase inhibitors is provided, which comprises contacting a cancer cell with a histone deacetylase inhibitor; comparing the distribution of a histone deacetylase in the cell after contacting with the distribution of the histone deacetylase in the cell before contacting or the distribution of the histone deacetylase in a control cell which has not been contacted with the compound to determine whether the contacting with the compound results in an increase in the relative concentration of histone deacetylase in the cytoplasm of the cell as compared to the nucleus of the cell; and wherein the susceptibility of the cancer is determined to be increased when the contacting results in an increase in the relative concentration of the histone deacetylase in the cytoplasm of the cell as compared to the nucleus of the cell.

DETAILED DESCRIPTION

Figure 1:
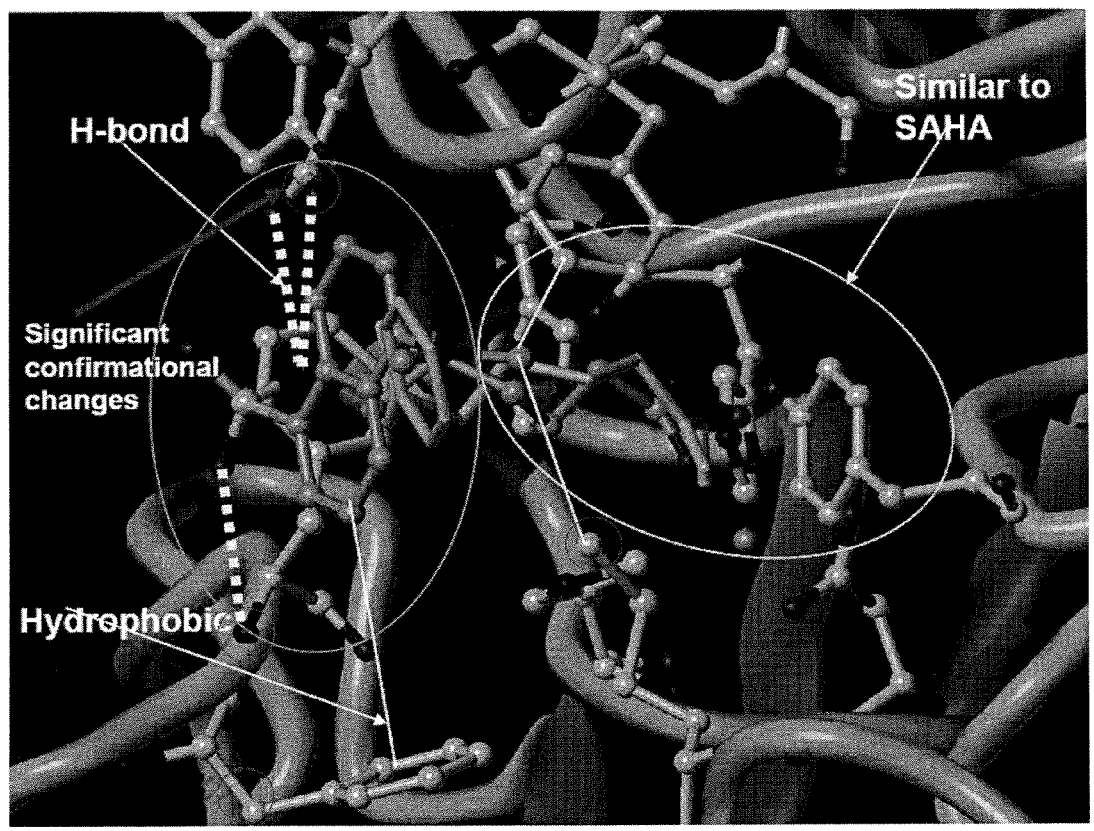
FIG. 1 shows the results of molecular modeling of the compound of Example 1 (6-(5-(dimethylamino)naphthalene-1-sulfonamido)-N-hydroxyhexanamide) and suberoylanilide hydroxamic acid into a model based on the HDAC8 X-ray structure with a molecular dynamic simulation of 50 ps. Potentially important molecular interactions are indicated with circles and arrows.

Provided herein are novel compounds that are active as histone deacetylase inhibitors. Certain of the novel compounds are fluorescent inhibitors of histone deacetylases. Some of the inhibitors exhibit pan-HDAC inhibition (e.g., as exhibiting in a pan-HDAC assay, see the Examples), while nonetheless retaining selectivity for a certain class (class II)

and/or certain isotype (HDAC6) of histone deacetylase. Also provided are novel methods of using the provided compounds, including methods of treatment and screening methods. Also provided are novel methods using fluorescent histone deacetylase inhibitors.

I. DEFINITIONS

A. General

As used in the specification and the appended claims, the singular forms "a," "an" and "the" include plural referents unless the context clearly dictates otherwise.

The term "contacting" means bringing at least two moieties together, whether in an in vitro system or an in vivo system.

The expression "effective amount", when used to describe an amount of compound or radiation applied in a method, refers to the amount of a compound that achieves the desired pharmacological effect or other effect, for example an amount that inhibits the abnormal growth or proliferation, or induces apoptosis of cancer cells, resulting in a useful effect.

The terms "treating" and "treatment" mean causing a therapeutically beneficial effect, such as ameliorating existing symptoms, preventing additional symptoms, ameliorating or preventing the underlying metabolic causes of symptoms, postponing or preventing the further development of a disorder and/or reducing the severity of symptoms that will or are expected to develop.

As used herein, "individual" (as in the subject of the treatment) means both mammals and non-mammals. Mammals include, for example, humans; non-human primates, e.g. apes and monkeys; cattle; horses; sheep; rats; mice; pigs; and goats. Non-mammals include, for example, fish and birds.

B. Chemical

In the following paragraphs some of the definitions include examples. The examples are intended to be illustrative, and not limiting.

The term "($C_1$-$C_y$)alkyl" (wherein x and y are integers) by itself or as part of another substituent means, unless otherwise stated, an alkyl group containing between x and y carbon atoms. An alkyl group formally corresponds to an alkane or cycloalkane with one C—H bond replaced by the point of attachment of the alkyl group to the remainder of the compound. An alkyl group may be straight-chained or branched. Alkyl groups having 3 or more carbon atoms may be cyclic. Cyclic alkyl groups having 7 or more carbon atoms may contain more than one ring and be polycyclic. Examples of straight-chained alkyl groups include methyl, ethyl, n-propyl, n-butyl, and n-octyl. Examples of branched alkyl groups include i-propyl, t-butyl, and 2,2-dimethylethyl. Examples of cyclic alkyl groups include cyclopentyl, cyclohexyl, cyclohexylmethyl, and 4-methylcyclohexyl. Examples of polycyclic alkyl groups include bicyclo[2.2.1]heptanyl, norbornyl, and adamantyl. Examples of ($C_x$-$C_y$)alkyl groups are ($C_1$-$C_6$) alkyl such as ($C_1$-$C_3$)alkyl, for example methyl and ethyl.

The term "($C_x$-$C_y$)alkylene" (wherein x and y are integers) refers to an alkylene group containing between x and y carbon atoms. An alkylene group formally corresponds to an alkane with two C—H bond replaced by points of attachment of the alkylene group to the remainder of the compound. Included are divalent straight hydrocarbon group consisting of methylene groups, such as, —$CH_2$—, —$CH_2CH_2$—, —$CH_2CH_2CH_2$—. In some embodiments, ($C_x$-$C_y$)alkylene may be ($C_1$-$C_6$)alkylene such as ($C_1$-$C_3$)alkylene.

The term "($C_x$-$C_y$) alkenyl" (wherein x and y are integers) denotes a radical containing x to y carbons, wherein at least one carbon-carbon double bond is present (therefore x must be at least 2). Some embodiments are 2 to 4 carbons, some embodiments are 2 to 3 carbons, and some embodiments have 2 carbons. Both E and Z isomers are embraced by the term "alkenyl." Furthermore, the term "alkenyl" includes di- and tri-alkenyls. Accordingly, if more than one double bond is present then the bonds may be all E or Z or a mixtures of E and Z. Examples of an alkenyl include vinyl, allyl, 2-butenyl, 3-butenyl, 2-pentenyl, 3-pentenyl, 4-pentenyl, 2-hexenyl, 3-hexenyl, 4-hexenyl, 5-hexanyl, 2,4-hexadienyl and the like.

The term "($C_x$-$C_y$) alkynyl" (wherein x and y are integers) denotes a radical containing 2 to 6 carbons and at least one carbon-carbon triple bond, some embodiments are 2 to 4 carbons, some embodiments are 2 to 3 carbons, and some embodiments have 2 carbons. Examples of an alkynyl include ethynyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. The term "alkynyl" includes di- and tri-ynes.

The term "($C_x$-$C_y$) alkoxy" (wherein x and y are integers) employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Embodiments include ($C_1$-$C_3$) alkoxy, such as ethoxy and methoxy.

The terms "halo" or "halogen" by themselves or as part of another substituent mean, unless otherwise stated, a fluorine, chlorine, bromine, or iodine atom, preferably, fluorine, chlorine, or bromine, more preferably, fluorine or chlorine.

The term "aliphatic hydrocarbon" refers to non-aromatic hydrocarbon groups, i.e. hydrocarbon groups lacking an aromatic ring. The term refers to hydrocarbon groups, wherein carbon atoms can be joined together in straight chains, branched chains, or rings and can be joined by single bonds, double bonds, or triple bonds, provided that none of the rings thereof is aromatic. Embodiments include aliphatic hydrocarbons, wherein carbon atoms are joined together only in straight chains and/or are joined only by single bonds. Preferred are alkyl and alkylene groups.

The term "oxygenated aliphatic hydrocarbon" refers to a group composed only of carbon, hydrogen, and oxygen atoms, wherein the carbon and oxygen atoms can be joined together in straight chains, branched chains, or rings and can be joined by single bonds, double bonds, or (in the case of carbon-carbon bonds) triple bonds, provided that none of the rings thereof is aromatic, and where carbon atoms thereof form the bonds to the remainder of the molecule. Included are those oxygenated aliphatic hydrocarbon groups, wherein carbon atoms are joined together only in straight chains and/or are joined only by single bonds. In some embodiments, oxygenated aliphatic hydrocarbon groups preferably contain at least twice as many carbon as oxygen atoms. Examples are ether and polyether groups, for example —$CH_2CH_2OCH_2CH_2$— and —$CH_2CH_2OCH_2CH_2OCH_2CH_2$—.

The term "aromatic" refers to a carbocycle or heterocycle having one or more polyunsaturated rings having aromatic character (i.e. having (4n+2) delocalized π (pi) electrons where n is an integer).

The term "aryl", employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples include phenyl; anthracyl; and naphthyl. Preferred are phenyl and naphthyl, most preferred is phenyl.

The term "heterocycle" or "heterocyclyl" or "heterocyclic" by itself or as part of another substituent means, unless otherwise stated, an unsubstituted or substituted, stable, mono- or multi-cyclic heterocyclic ring system which consists of carbon atoms and at least one heteroatom selected from the group consisting of N, O, and S, wherein the nitrogen and sulfur heteroatoms may be optionally oxidized, and the nitrogen atom may be optionally quaternized. The heterocyclic system may be attached, unless otherwise stated, at any heteroatom or carbon atom which affords a stable structure.

The term "heteroaryl" or "heteroaromatic" refers to a heterocycle having aromatic character. A polycyclic heteroaryl may include one or more rings which are partially saturated. Examples include tetrahydroquinoline and 2,3-dihydrobenzofuryl. For compounds of formula I, the attachment point on ring $Ar^1$ or $Ar^2$ is understood to be on an atom which is part of an aromatic monocyclic ring or a ring component of a polycyclic aromatic which is itself an aromatic ring.

Examples of non-aromatic heterocycles include monocyclic groups such as: aziridine, oxirane, thiirane, azetidine, oxetane, thietane, pyrrolidine, pyrroline, imidazoline, pyrazolidine, dioxolane, sulfolane, 2,3-dihydro furan, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include: pyridyl, pyrazinyl, pyrimidinyl, particularly 2- and 4-pyrimidinyl, pyridazinyl, thienyl, furyl, pyrrolyl, particularly 2-pyrrolyl, imidazolyl, thiazolyl, oxazolyl, pyrazolyl, particularly 3- and 5-pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include: indolyl, particularly 3-, 4-, 5-, 6- and 7-indolyl, indolinyl, quinolyl, tetrahydroquinolyl, isoquinolyl, particularly 1- and 5-isoquinolyl, 1,2,3,4-tetrahydroisoquinolyl, cinnolinyl, quinoxalinyl, particularly 2- and 5-quinoxalinyl, quinazolinyl, phthalazinyl, 1,5-naphthyridinyl, 1,8-naphthyridinyl, 1,4-benzodioxanyl, coumarin, dihydrocoumarin, benzofuryl, particularly 3-, 4-, 5-, 6- and 7-benzofuryl, 2,3-dihydrobenzofuryl, 1,2-benzisoxazolyl, benzothienyl, particularly 3-, 4-, 5-, 6-, and 7-benzothienyl, benzoxazolyl, benzthiazolyl, particularly 2-benzothiazolyl and 5-benzothiazolyl, purinyl, benzimidazolyl, particularly 2-benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

The term "substituted" means that an atom or group of atoms formally replaces hydrogen as a "substituent" attached to another group. For aryl and heteroaryl groups, the term "substituted", unless otherwise indicated, refers to any level of substitution, namely mono-, di-, tri-, tetra-, or penta-substitution, where such substitution is permitted. The substituents are independently selected, and substitution may be at any chemically accessible position.

The "valency" of a chemical group refers to the number of bonds by which it is attached to other groups of the molecule.

II. NOVEL COMPOUNDS

In one aspect, provided herein is a compound according to formula I:

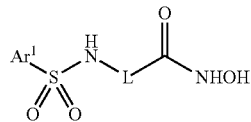

or a salt thereof;
wherein:
-L- is a divalent aliphatic hydrocarbon or oxygenated hydrocarbon linking group comprising a chain of 4, 5, 6, 7, or 8 atoms as the shortest chain of atoms separating its attachment points, wherein the atoms forming the bonds to the remainder of the molecule are carbon atoms;

$Ar^1$ is selected from the group consisting of unsubstituted or substituted naphthyl and unsubstituted or substituted fused bicyclic heteroaryl, wherein the substituents of the naphthyl or bicyclic heteroaryl are selected from the group consisting of —$R^1$; —$Ar^2$; —($C_1$-$C_3$)alkylene-$Ar^2$; ($C_2$-$C_6$)alkenyl; ($C_2$-$C_6$)alkynyl; halogen; —C≡N; —$NO_2$; —C(=O)$R^3$; —C(=O)O$R^3$; —C(=O)$NR^4_2$; —C(=$NR^3$)$NR^4_2$; —$OR^2$; —OC(=O)($C_1$-$C_6$)alkyl; —OC(=O)($C_1$-$C_6$)alkylene-$R^5$; —OC(=O)O($C_1$-$C_6$)alkyl; —OC(=O)$NR^4_2$; —$NR^4_2$; —$NR^4$C(=O)$R^3$; —$NR^4$C(=O)$Ar^2$; —$NR^4$C(=O)O($C_1$-$C_6$)alkyl; —$NR^4$C(=O)$NR^4_2$; —$NR^4SO_2R^3$; —$NR^4SO_2Ar^2$; —$SR^2$; —S(O)$R^2$; —$SO_2R^2$; —$OSO_2$($C_1$-$C_6$)alkyl; —$OSO_2Ar^2$; and —$SO_2NR^4_2$;

each $R^1$ is independently unsubstituted ($C_1$-$C_6$)alkyl or ($C_1$-$C_6$)alkyl substituted with up to five halogen atoms and up to two substituents selected from the group consisting of —CN; —C(=O)$R^3$; —C(=O)O$R^3$; —C(=O)$NR^4_2$; —$OR^3$; —OC(=O)($C_1$-$C_6$)alkyl; —OC(=O)O($C_1$-$C_6$)alkyl; —OC(=O)$NR^4_2$; —$NR^4_2$; —$NR^3$C(=O)$R^3$; —$NR^3$C(=O)$NR^4_2$; —S($C_1$-$C_6$)alkyl; —S(O)($C_1$-$C_6$)alkyl; and —$SO_2$($C_1$-$C_6$)alkyl;

each $R^2$ is independently selected from the group consisting of hydrogen, $R^1$, $Ar^2$ and ($C_1$-$C_3$)alkylene-$Ar^2$;

each $R^3$ is independently hydrogen or ($C_1$-$C_6$)alkyl;

each $R^4$ is independently hydrogen; ($C_1$-$C_6$)alkyl; —($C_2$-$C_6$)alkylene-$OR^3$; —($C_1$-$C_6$)alkylene-C(=O)$OR^3$; —($C_1$-$C_6$)alkylene-OC(=O)$R^3$; —($C_2$-$C_6$)alkylene-$NR^6_2$; —($C_1$-$C_6$)alkylene-C(=O)$NR^6_2$; ($C_1$-$C_6$)alkylene-$NR^3$C(=O)$R^3$; —($C_1$-$C_6$)alkylene-$NR^3$C(=O)$NR^6_2$; $Ar^2$, or —($C_1$-$C_3$)-alkylene$Ar^2$; or, optionally, within any occurrence of $NR^4_2$, independently of any other occurrence of $NR^4_2$, the two $R^4$ groups in combination are —$(CH_2)_a$— or —$(CH_2)_b$A$(CH_2)_2$—;

each $R^5$ is independently $Ar^2$ or 1,4-benzoquinon-2-yl optionally substituted with 0, 1, 2, or 3 alkyl groups;

each $R^6$ is independently hydrogen; ($C_1$-$C_6$)alkyl; —($C_2$-$C_6$)alkylene-$OR^3$; —($C_1$-$C_6$)alkylene-C(=O)$OR^3$; —($C_1$-$C_6$)alkylene-OC(=O)$R^3$; ($C_2$-$C_6$)alkylene-$NR^3_2$; —($C_1$-$C_6$)alkylene-C(=O)$NR^3_2$; —($C_1$-$C_6$)alkylene-$NR^3$C(=O)$R^3$; —($C_1$-$C_6$)alkylene$NR^3$C(=O)$NR^3_2$; —$Ar^2$, or —($C_1$-$C_3$)alkylene-$Ar^2$; or, optionally, within any occurrence of $NR^6_2$, independently of any other occurrence of $NR^6_2$, the two $R^6$ groups in combination are —$(CH_2)_a$— or —$(CH_2)_b$A$(CH_2)_2$—;

each a is independently selected from the group consisting of 4, 5, and 6;

each b is independently selected from the group consisting of 2 and 3;

each A is independently selected from the group consisting of O, S, $NR^3$; NC(=O)$R^3$; $NSO_2R^3$; N($C_2$-$C_6$)alkylene-$OR^3$; N($C_1$-$C_6$)alkylene-C(=O)$OR^3$; N($C_1$-$C_6$)alkylene-OC(=O)$R^3$; N($C_2$-$C_6$)alkylene-$NR^3_2$; N($C_1$-$C_6$)alkylene-C (=O)NR³₂; N(C₁-C₆)alkylene-NR³C(=O)R³; N(C₁-C₆)alkylene-NR³C(=O)NR³₂; NAr²; N(C₁-C₃)alkylene-Ar²; and NC(=O)Ar²;

each Ar² is independently selected from the group consisting of unsubstituted aryl, unsubstituted heteroaryl, and aryl or heteroaryl substituted with one or more substituents independently selected from the group consisting of (C₁-C₆)alkyl; (C₂-C₆)alkenyl; (C₂-C₆)alkynyl; halogen; —C≡N; —NO₂; —C(=O)R³; —C(=O)OR³; —C(=O)NR³₂; —C(=NR³) NR³₂; —OR³; —OC(=O)(C₁-C₆)alkyl; —OC(=O)O(C₁-C₆)alkyl; —OC(=O)NR³₂; —NR³₂; —NR³C(=O)R³; —NR³C(=O)O(C₁-C₆)alkyl; —NR³C(=O)NR³₂; —S(C₁-C₆)alkyl; —S(O)(C₁-C₆)alkyl; and —SO₂(C₁-C₆)alkyl; —SO₂NR³₂; and (C₁-C₃)perfluoroalkyl.

When it is stated of the group -L- that it "comprises a chain of 4, 5, 6, 7, or 8 atoms separating its attachment points," it is meant that the shortest chain of atoms linking the attachment points of the group -L- to the rest of the molecule is a chain of 4, 5, 6, 7, or 8 atoms. Preferably, the shortest chain of atoms linking the attachment points of the group -L- to the rest of the molecule is a chain of either 5 or 6 atoms. The "attachment points" are the bonds linking the group L to the rest of the molecule (i.e. all of the atoms in the group L forming the chain between the two bonds are counted). For example, the following (exemplary) linking groups have the following numbers of atoms in the shortest chain of atoms linking its attachment points:

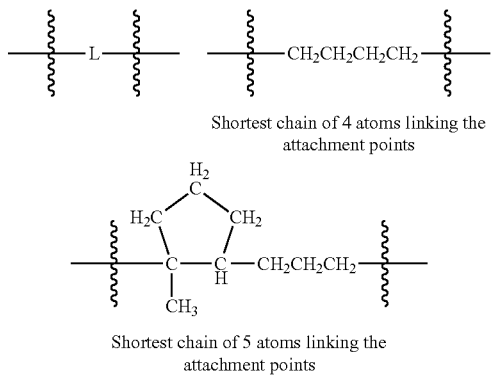

Shortest chain of 4 atoms linking the attachment points

Shortest chain of 5 atoms linking the attachment points

Embodiments of the compounds according to formula I include those wherein -L- is a hydrocarbon linking group, such as an alkylene group, for example —(CH₂)ₙ—, wherein n is 4, 5, 6, 7 or 8. In certain embodiments, n is 5 or 6.

Other embodiments of the compounds according to formula I include those wherein Ar¹ is substituted or unsubstituted naphthyl. In some sub-embodiments thereof, Ar¹ is substituted or unsubstituted 1-naphthyl. In some sub-embodiments thereof, Ar¹ is substituted naphthyl, and in some sub-embodiments thereof, Ar¹ is substituted 1-naphthyl. In other sub-embodiments, Ar¹ is monosubstituted naphthyl, such as monosubstituted 1-naphthyl.

In some embodiments, the substituents of Ar¹ are —OR²; —OC(=O)(C₁-C₆)alkyl; —OC(=O)(C₁-C₆)alkylene-R⁵; —OC(=O)O(C₁-C₆)alkyl; —OC(=O)NR⁴₂; —NR⁴₂; —NR⁴C(=O)R³; —NR⁴C(=O)Ar²; —NR⁴C(=O)O(C₁-C₆)alkyl; —NR⁴C(=O)NR⁴₂; —NR⁴SO₂R³; —NR⁴SO₂Ar²; —SR²; —OSO₂(C₁-C₆)alkyl; and —OSO₂Ar². In some cases, Ar¹ is substituted 1-naphthyl, wherein the 5-position of the 1-naphthyl is substituted by a substituent selected from the group consisting of —OR²; —OC(=O)(C₁-C₆)alkyl; —OC(=O)(C₁-C₆)alkylene-R⁵; —OC(=O)O(C₁-C₆)alkyl; —OC(=O)NR⁴₂; —NR⁴₂; —NR⁴C(=O)R³; —NR⁴C(=O)Ar²; —NR⁴C(=O)O(C₁-C₆)alkyl; —NR⁴C(=O)NR⁴₂; —NR⁴SO₂R³; —NR⁴SO₂Ar²; —SR²; —OSO₂(C₁-C₆)alkyl; and —OSO₂Ar². In some embodiments, Ar¹ is monosubstituted 1-naphthyl, wherein the 5-position of the 1-naphthyl is substituted by a substituent selected from the group consisting of —OR²; —OC(=O)(C₁-C₆)alkyl; —OC(=O)(C₁-C₆)alkylene-R⁵; —OC(=O)O(C₁-C₆)alkyl; —OC(=O)NR⁴₂; —R⁴₂; —NR⁴C(=O)R³; —NR⁴C(=O)Ar²; —NR⁴C(=O)O(C₁-C₆)alkyl; —NR⁴C(=O)NR⁴₂; —NR⁴SO₂R³; —NR⁴SO₂Ar²; —SR²; —OSO₂(C₁-C₆)alkyl; and —OSO₂Ar².

In certain embodiments, the substituents of Ar¹ are —OR² and —NR⁴₂. In some cases, Ar¹ is substituted 1-naphthyl, wherein the 5-position of the 1-naphthyl is substituted by a substituent selected from the group consisting of —OR² and —NR⁴₂. In other cases, Ar¹ is monosubstituted 1-naphthyl, wherein the 5-position of the 1-naphthyl is substituted by a substituent selected from the group consisting of —OR² and —NR⁴₂. In some embodiments, the substituent can hydrogen bond with a histone deacetylase, e.g., the histone deacetylase for which the compound is inhibitory.

In other embodiments, the substituents of Ar¹ are —OH, O(C₁-C₆)alkyl, —NH₂, —NH(C₁-C₆)alkyl, and —N((C₁-C₆)alkyl)₂. Some embodiments are wherein Ar¹ is substituted 1-naphthyl, wherein the 5-position of the 1-naphthyl is substituted by a substituent selected from the group consisting of —OH, O(C₁-C₆)alkyl, —NH₂, —NH(C₁-C₆)alkyl, and —N((C₁-C₆)alkyl)₂. Other embodiments are those wherein Ar¹ is monosubstituted 1-naphthyl, wherein the 5-position of the 1-naphthyl is substituted by a substituent selected from the group consisting of —OH, O(C₁-C₆)alkyl, —NH₂, —NH(C₁-C₆)alkyl, and —N((C₁-C₆)alkyl)₂.

Other substituents of Ar¹ are —NR⁴₂, such as —NH₂, —NH(C₁-C₆)alkyl, and —N((C₁-C₆)alkyl)₂. Ar¹ may be substituted 1-naphthyl, wherein the 5-position of the 1-naphthyl is substituted by a substituent selected from the group consisting of —NR⁴₂, such as —NH₂, —NH(C₁-C₆)alkyl, and —N((C₁-C₆)alkyl)₂. Ar¹ may also be monosubstituted 1-naphthyl, wherein the 5-position of the 1-naphthyl is substituted by a substituent selected from the group consisting of —NR⁴₂, such as —NH₂, —NH(C₁-C₆)alkyl, and —N((C₁-C₆)alkyl)₂. In some embodiment the alkyl group is methyl or ethyl, and in other embodiments is methyl.

Embodiments of the compounds according to formula I include those wherein Ar¹ is substituted by substituents as defined in the embodiments above, and wherein -L- is a hydrocarbon linking group, such as an alkylene group, which may be —(CH₂)₆—, wherein n is 4, 5, 6, 7 or 8, and in particular 5 or 6.

Other embodiments of the compounds according to formula I are those which are fluorescent. The fluorescence is preferably in the visible spectrum.

Particular compounds that are fluorescent embodiments of the compounds according to formula I include:

6-(5-(dimethylamino)naphthalene-1-sulfonamido)-N-hydroxypentanamide
6-(5-(dimethylamino)naphthalene-1-sulfonamido)-N-hydroxyhexanamide
6-(5-(dimethylamino)naphthalene-1-sulfonamido)-N-hydroxyheptanamide; and
6-(5-(dimethylamino)naphthalene-1-sulfonamido)-N-hydroxyoctanamide; and salts of any thereof.

III. SALTS

The compounds according to formula I, any of the embodiments thereof, as well as intermediates used in making compounds according to formula I may take the form of salts. The term "salts" embraces addition salts of free acids or free bases which are compounds described herein. The term "pharmaceutically-acceptable salt" refers to salts which possess toxicity profiles within a range that affords utility in pharmaceutical applications. Pharmaceutically unacceptable salts may nonetheless possess properties such as high crystallinity, which may render them useful, for example in processes of synthesis, purification or formulation of compounds described herein. In general the useful properties of the compounds described herein do not depend critically on whether the compound is or is not in a salt form, so unless clearly indicated otherwise (such as specifying that the compound should be in "free base" or "free acid" form), reference in the specification to compounds of formula I should be understood as encompassing salts of the compound, whether or not this is explicitly stated.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts.

All of these salts may be prepared by conventional means from the corresponding compound according to formula I by reacting, for example, the appropriate acid or base with the compound according to formula I. Preferably the salts are in crystalline form, and preferably prepared by crystallization of the salt from a suitable solvent. The person skilled in the art will know how to prepare and select suitable salts for example, as described in *Handbook of Pharmaceutical Salts Properties, Selection, and Use* By P. H. Stahl and C. G. Wermuth (Wiley-VCH 2002).

IV. SOLVATE FORMS

The compounds according to formula I, and salts thereof as well as intermediates used in making compounds according to formula I, and salts thereof may take the form of solvates, including hydrates. In general, the useful properties of the compounds described herein are not believed to depend critically on whether the compound or salt thereof is or is not in the form of a solvate.

V. PRODRUGS

The compounds according to formula I, and salts thereof as well as intermediates used in making compounds according to formula I, and salts thereof, may be administered in the form of prodrugs. By "prodrug" is meant for example any compound (whether itself active or inactive) that is converted chemically in vivo into a biologically active compound of the formula I following administration of the prodrug to a patient.

Generally a "prodrug" is a covalently bonded carriers which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds according to formula I. Specifically, conjugates such as β-glucuronides and β-galactosides have been suggested as prodrugs of hydroxamates. See Thomas, et al., *Bioorg. Med. Chem. Lett.,* 2007, 983-986.

The suitability and techniques involved in making and using prodrugs are well known by those skilled in the art. Preparation and use of prodrugs is discussed in T. Higuchi and V. Stella, "Pro-drugs as Novel Delivery Systems," Vol. 14 of the ACS Symposium Series, and in Bioreversible Carriers in Drug Design, ed. Edward B. Roche, American Pharmaceutical Association and Pergamon Press, 1987, both of which are hereby incorporated by reference in their entirety.

VI. STEREOCHEMISTRY, TAUTOMERISM, AND CONFORMATIONAL ISOMERISM

The compounds provided for by formula I may encompass various stereochemical forms and tautomers. The formula also encompasses diastereomers as well as optical isomers, e.g. mixtures of enantiomers including racemic mixtures, as well as individual enantiomers and diastereomers, which arise as a consequence of structural asymmetry in certain compounds of formula I. Separation of the individual isomers or selective synthesis of the individual isomers is accomplished by application of various methods which are well known to practitioners in the art.

A. Geometrical Isomerism

Certain compounds of formula I possess an olefinic double bond. The stereochemistry of compounds possessing an olefinic double bond is designated using the nomenclature using E and Z designations. The compounds are named according to the Cahn-Ingold-Prelog system, described in the IUPAC 1974 Recommendations, Section E: Stereochemistry, in *Nomenclature of Organic Chemistry*, John Wiley & Sons, Inc., New York, N.Y., 4$^{th}$ ed., 1992, pp. 127-38, the entire contents of which is incorporated herein by reference.

B. Optical Isomerism

Certain compounds of formula I may contain one or more chiral centers, and may exist in, and may be isolated as pure enantiomeric or diastereomeric forms or as racemic mixtures. Formula I therefore encompasses any possible enantiomers, diastereomers, racemates or mixtures thereof which are biologically active in the inhibiting histone deacetylase.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system.

Formula I encompasses diastereomers as well as their racemic and resolved, diastereomerically and enantiomerically pure forms and salts thereof. Diastereomeric pairs may be resolved by known separation techniques including normal and reverse phase chromatography, and crystallization.

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Isolated optical isomers may be purified from racemic mixtures by well-known chiral separation techniques. According to one such method, a racemic mixture of a compound having the structure of formula I, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

C. Conformational Isomerism

Due to chemical properties such as resonance lending some double bond character to a C—N bond, it is possible that individual conformers of certain compounds of formula I may be observable and even separable under certain circumstances. Formula I therefore includes any possible stable rotamers of formula I which are biologically active in inhibiting histone deacetylase.

D. Tautomerism

Certain compounds of the invention may exist in tautomeric forms, which differ by the location of a hydrogen atom and typically are in rapid equilibrium. In such circumstances, molecular formulae drawn will typically only represent one of the possible tautomers even though equilibration of these tautomeric forms will occur in equilibrium in the compound. Examples include keto-enol tautomerism and amide-imidic acid tautomerism. Tautomerism is frequently also seen in heterocyclic compounds. All tautomeric forms of the compounds according to formula I are to be understood as being included within the scope of the formula.

VII. PHARMACEUTICAL COMPOSITIONS

The compounds of formula I may be administered in the form of a pharmaceutical composition, in combination with a pharmaceutically acceptable carrier. The active ingredient in such formulations may comprise from 0.1 to 99.99 weight percent. "Pharmaceutically acceptable carrier" means any carrier, diluent or excipient which is compatible with the other ingredients of the formulation and not deleterious to the recipient.

The active agent may be administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington: The Science and Practice of Pharmacy,* 20th Edition (2003), Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or non-aqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The specific dose of a compound according to formula I required to obtain therapeutic benefit in the methods of treatment described herein will, of course, be determined by the particular circumstances of the individual patient including the size, weight, age and sex of the patient, the nature and stage of the disease being treated, the aggressiveness of the disease disorder, and the route of administration of the compound.

For example, a daily dosage from about 0.05 to about 50 mg/kg/day may be utilized, for example a dosage from about 0.1 to about 10 mg/kg/day. Higher or lower doses are also contemplated as it may be necessary to use dosages outside these ranges in some cases. The daily dosage may be divided, such as being divided equally into two to four times per day daily dosing. The compositions may be formulated in a unit dosage form, each dosage containing from about 1 to about 500 mg, more typically, about 10 to about 100 mg of active agent per unit dosage. The term "unit dosage form" refers to physically discrete units suitable as a unitary dosage for human subjects and other mammals, each unit containing a predetermined quantity of active material calculated to produce the desired therapeutic effect, in association with a suitable pharmaceutical excipient.

The pharmaceutical compositions described herein may also be formulated so as to provide slow or controlled release of the active ingredient therein using, for example, hydropropylmethyl cellulose in varying proportions to provide the desired release profile, other polymer matrices, gels, permeable membranes, osmotic systems, multilayer coatings, microparticles, liposomes and/or microspheres.

In general, a controlled-release preparation is a pharmaceutical composition capable of releasing the active ingredient at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations.

U.S. Pat. No. 5,674,533 discloses controlled-release pharmaceutical compositions in liquid dosage forms for the administration of moguisteine, a potent peripheral antitussive. U.S. Pat. No. 5,059,595 describes the controlled-release of active agents by the use of a gastro-resistant tablet for the therapy of organic mental disturbances. U.S. Pat. No. 5,591, 767 describes a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 describes controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. Biodegradable microparticles are known for use in controlled-release formulations. U.S. Pat. No. 5,354,566 discloses a controlled-release powder that contains the active ingredient. U.S. Pat. No. 5,733,566 describes the use of polymeric microparticles that release antiparasitic compositions.

The controlled-release of the active ingredient may be stimulated by various inducers, for example pH, temperature, enzymes, water, or other physiological conditions or compounds. Various mechanisms of drug release exist. For example, in one embodiment, the controlled-release component may swell and form porous openings large enough to release the active ingredient after administration to a patient. The term "controlled-release component" means a compound or compounds, such as polymers, polymer matrices, gels, permeable membranes, liposomes and/or microspheres that facilitate the controlled-release of the active ingredient in the pharmaceutical composition. In another embodiment, the controlled-release component is biodegradable, induced by exposure to the aqueous environment, pH, temperature, or enzymes in the body. In another embodiment, sol-gels may be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

VIII. METHODS OF SYNTHESIS AND USEFUL INTERMEDIATES

Processes for preparing compounds according to formula I, intermediates that are useful in the preparation of such compounds, and processes for preparing such intermediates are also provided herein.

In the text, formulae and schemes that follow, unless otherwise indicated $Ar^1$ and L are as defined above for formula I.

Compounds of formula I may be prepared from compounds of formula II, wherein X represents a suitable leaving group, by reaction with a compound of formula III, wherein Y is hydrogen or a suitable oxygen protecting group, using a suitable acylation procedure, followed, if Y is a protecting group, by deprotection, as illustrated in Scheme 1.

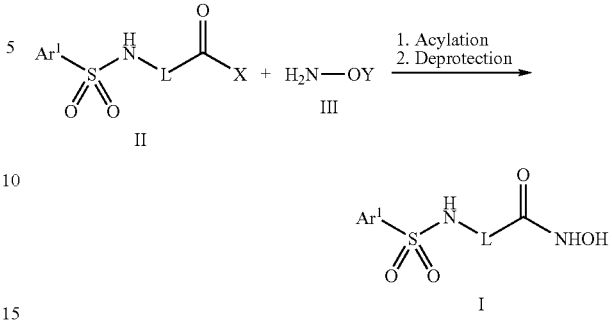

Suitable leaving groups X include: OH, halogen, OAlkyl, OAryl, OC(=O)Alkyl, OC(=O)Aryl. A suitable acylation procedure involves treatment of a compound of formula II with a compound of formula III at about 0-120° C. in a suitable solvent. The presence of a base, or, when X=OH, a coupling agent, may also be necessary for the reaction to occur. Suitable bases for the reaction include: 4-(N,N-dimethylamino)pyridine, pyridine, triethylamine, N,N-diisopropylethylamine. The preferred base is dimethylaminopyridine. Suitable coupling agents when X=OH include: carbodiimides, for example 1,3-dicyclohexylcarbodiimide or 1-(3-dimethylaminopropyl-3-ethylcarbodiimide hydrochloride; phosphonium reagents, for example benzotriazol-1-yloxytris(dimethylamino)phosphonium hexafluorophosphate or benzotriazol-1-yloxytripyrrolidinophosphonium hexafluorophosphate; and uronium reagents, for example O-benzotriazol-1-yl-N,N,N',N'-tetramethyluronium tetrafluoroborate. The preferred coupling agents are carbodiimides, for example 1,3-dicyclohexylcarbodiimide. Suitable solvents for the reaction include amide solvents such as N,N-dimethylformamide, dimethylsulfoxide, ether solvents such as tetrahydrofuran, or halogenated hydrocarbons such as chloroform. The preferred solvent is N,N-dimethylformamide. The reaction is preferably performed at a temperature of 0-50° C., and most preferably at a temperature of 20-30° C.

Suitable protecting hydroxyl protecting groups Y are well known in the art and include ether groups such as benzyl and t-butyl, and silyl groups such as t-butyldimethylsilyl as are suitable deprotection methods. The preferred protecting group is benzyl, wherein deprotection may be achieved by catalytic hydrogenation, for example using palladium on carbon in an alcohol solvent (e.g. methanol).

Alternatively, compounds of formula I may be prepared from compounds of formula IV, wherein X represents a suitable leaving group, by reaction with a compound of formula V, wherein Y is hydrogen or a suitable oxygen protecting group, using a suitable sulfonylation procedure, followed, if Y is a protecting group, by deprotection, as illustrated in Scheme 2.

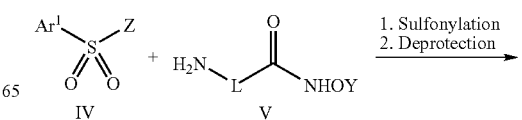

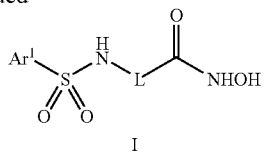

I

Suitable leaving groups Z include: halogen, preferably chlorine, and OAryl. A suitable sulfonylation procedure involves treatment of a compound of formula V with a compound of formula IV at about 0-120° C. in a suitable solvent. The presence of a base may be necessary for the reaction to occur. Suitable bases for the reaction include: 4-(N,N-dimethylamino)pyridine, pyridine, triethylamine, N,N-diisopropylethylamine. The preferred base is triethylamine. Suitable solvents for the reaction include ketone solvents such as acetone, amide solvents such as N,N-dimethylformamide, dimethylsulfoxide, ether solvents such as tetrahydrofuran, or halogenated hydrocarbons such as chloroform. The preferred solvent is acetone. The reaction is preferably performed at a temperature of 0-50° C., and most preferably at a temperature of 20-30° C. Suitable hydroxyl protecting groups Y and suitable deprotection methods are as described above.

Compounds of formula II, wherein X is other than OH may be prepared from compounds of formula II, wherein X represents OH by methods which are well known in the art. For example, compounds according to formula II, wherein X is chlorine may be prepared by reacting a compound according to formula II, wherein X is OH by reaction with thionyl chloride.

Compounds of formula II, wherein X is OH may be prepared by reaction of a compound according to formula VI, wherein X is OH (or a suitable protected faun thereof, for example an ester) with a compound of formula IV, wherein Z is a suitable leaving group using a suitable sulfonylation procedure, as illustrated in Scheme 3. The suitable leaving groups and conditions for forming the reaction are as described for the sulfonylation reaction of the compounds according to formula V, as described above.

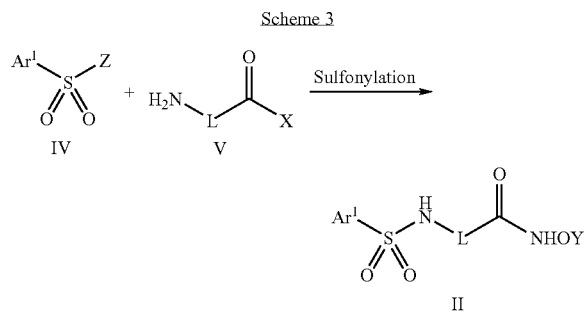

Compounds of formula VI may be prepared from compounds of formula VII, wherein X represents a suitable leaving group and Q represents a suitable amine protecting group, by reaction with a compound of formula III, wherein Y is hydrogen or a suitable oxygen protecting group, using a suitable acylation procedure, followed by deprotection of the amino group, as illustrated in Scheme 4. Suitable leaving groups X and protecting groups Y are as described for the acylation reaction of the compounds according to formula II as described above. Suitable amine protecting groups are well known in the art, and include, for example, carbonate groups such as t-butyloxycarbonyl, as are conditions for introducing such groups (i.e. preparing a compound according to formula VII from a compound according to formula VI) and removing such groups. For example, a t-butyloxycarbonyl (BOC) group may be introduced by reaction of an amine with di-t-butyldicarbonate ("BOC anhydride") or 2-(t-butoxycarbonyloxy-imino)-2-phenylacetonitrile ("BOC-on"), and removed by mild acid hydrolysis.

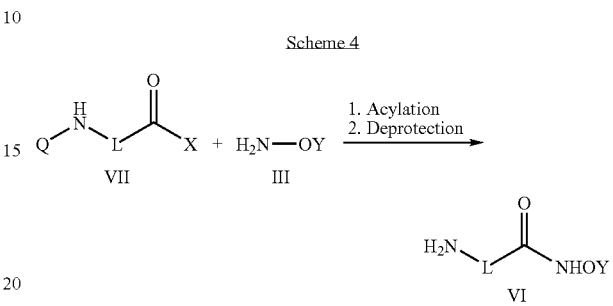

The compounds according to formula III are either commercially available, known in the art or may be prepared by methods which are known to the person skilled in the art. For example, O-benzylhydroxylamine is commercially available, for example from Aldrich Chemical Company (sold as the hydrochloride salt).

The compounds according to formula IV are either commercially available, known in the art or may be prepared by methods which are known to the person skilled in the art. For example, sulfonyl chlorides may be prepared by the chlorosulfonation of aromatic compounds, or by the chlorination of various aromatic derivatives (e.g. Johnson, *Proc. Natl. Acad. Sci. USA*, 1939, 25(9): 448-452). For a discussion of the synthesis of sulfonyl chlorides, see, for example G. Hilgetag and A. Martini, *Preparative Organic Chemistry* (J. Wiley and Sons, 1972) p. 670, U.S. Pat. Nos. 5,387,681, and 6,140,505 and the references cited therein.

The compounds according to formula VII are either commercially available, known in the art or may be prepared by methods which are known to the person skilled in the art. For example, 5-aminopentanoic acid (5-aminovaleric acid), 6-amionhexanoic acid (6-aminocaproic acid), 7-aminoheptanoic acid (7-aminoenanthic acid) and 8-amionoctanoic acid (8-amioncaprylic acid) are all commercially available, for example from Aldrich Chemical Company.

The above-described reactions, unless otherwise noted, are usually conducted at a pressure of about one to about three atmospheres, preferably at ambient pressure (about one atmosphere).

In some embodiments, the compounds according to formula I may be, or may be used as isolated compounds. The expression "isolated compound" refers to a preparation of a compound of formula I, or a mixture of compounds according to formula I, wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of formula I or a mixture of compounds according to formula I, which contains the named compound or mixture of compounds according to formula I in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds of formula I and intermediates may be isolated from their reaction mixtures and purified by standard techniques such as filtration, liquid-liquid extraction, solid phase extraction, distillation, recrystallization or chromatography, including flash column chromatography, or HPLC. The preferred method for purification of the compounds according to formula I or salts thereof comprises crystallizing the compound or salt from a solvent to form, preferably, a crystalline form of the compounds or salts thereof. Following crystallization, the crystallization solvent is removed by a process other than evaporation, for example filtration or decanting, and the crystals are then preferably washed using pure solvent (or a mixture of pure solvents). Suitable solvents for crystallization include water, alcohols, particularly alcohols containing up to four carbon atoms such as methanol, ethanol, isopropanol, and butan-1-ol, butan-2-ol, and 2-methyl-2-propanol, ethers, for example diethyl ether, diisopropyl ether, t-butyl methyl ether, 1,2-dimethoxyethane, tetrahydrofuran and 1,4-dioxane, carboxylic acids, for example formic acid and acetic acid, and hydrocarbon solvents, for example pentane, hexane, toluene, and mixtures thereof, particularly aqueous mixtures such as aqueous ethanol. Pure solvents, preferably at least analytical grade, and more preferably pharmaceutical grade are preferably used. In a preferred embodiment of the processes, the products are so isolated. In the compounds according to formula I or salt thereof, and pharmaceutical compositions thereof, the compound according to formula I or salt thereof is preferably in or prepared from a crystalline form, preferably prepared according to such a process.

It will be appreciated by one skilled in the art that certain aromatic substituents in the compounds of formula I, intermediates used in the processes described above, or precursors thereto, may be introduced by employing aromatic substitution reactions to introduce or replace a substituent, or by using functional group transformations to modify an existing substituent, or a combination thereof. Such reactions may be effected either prior to or immediately following the processes mentioned above. The reagents and reaction conditions for such procedures are known in the art. Specific examples of procedures which may be employed include, but are not limited to, electrophilic functionalization of an aromatic ring, for example via nitration, halogenation, or acylation; transformation of a nitro group to an amino group, for example via reduction, such as by catalytic hydrogenation; acylation, alkylation, or sulfonylation of an amino or hydroxyl group; replacement of an amino group by another functional group via conversion to an intermediate diazonium salt followed by nucleophilic or free radical substitution of the diazonium salt; or replacement of a halogen by another group, for example via nucleophilic or organometallically-catalyzed substitution reactions.

Additionally, in the aforesaid processes, certain functional groups which would be sensitive to the reaction conditions may be protected by protecting groups. A protecting group is a derivative of a chemical functional group which would otherwise be incompatible with the conditions required to perform a particular reaction which, after the reaction has been carried out, can be removed to re-generate the original functional group, which is thereby considered to have been "protected". Any chemical functionality that is a structural component of any of the reagents used to synthesize compounds described herein may be optionally protected with a chemical protecting group if such a protecting group is useful in the synthesis of compounds described herein. The person skilled in the art knows when protecting groups are indicated, how to select such groups, and processes that can be used for selectively introducing and selectively removing them, because methods of selecting and using protecting groups have been extensively documented in the chemical literature. Techniques for selecting, incorporating and removing chemical protecting groups may be found, for example, in *Protective Groups in Organic Synthesis* by Theodora W. Greene, Peter G. M. Wuts, John Wiley & Sons Ltd., the entire disclosure of which is incorporated herein by reference.

In addition to use of a protecting group, sensitive functional groups may be introduced as synthetic precursors to the functional group desired in the intermediate or final product. An example of this is an aromatic nitro ($-NO_2$) group. The aromatic nitro group goes not undergo any of the nucleophilic reactions of an aromatic amino group. However, the nitro group can serve as the equivalent of a protected amino group because it is readily reduced to the amino group under mild conditions that are selective for the nitro group over most other functional groups.

It will be appreciated by one skilled in the art that the processes described are not the exclusive means by which compounds described herein may be synthesized and that an extremely broad repertoire of synthetic organic reactions is available to be potentially employed in synthesizing those compounds. The person skilled in the art knows how to select and implement appropriate synthetic routes. Suitable synthetic methods may be identified by reference to the literature, including reference sources such as *Comprehensive Organic Synthesis*, Ed. B. M. Trost and I. Fleming (Pergamon Press, 1991), *Comprehensive Organic Functional Group Transformations*, Ed. A. R. Katritzky, O. Meth-Cohn, and C. W. Rees (Pergamon Press, 1996), *Comprehensive Organic Functional Group Transformations II*, Ed. A. R. Katritzky and R. J. K. Taylor (Editor) (Elsevier, $2^{nd}$ Edition, 2004), *Comprehensive Heterocyclic Chemistry*, Ed. A. R. Katritzky and C. W. Rees (Pergamon Press, 1984), and *Comprehensive Heterocyclic Chemistry II*, Ed. A. R. Katritzky, C. W. Rees, and E. F. V. Scriven (Pergamon Press, 1996).

IX. METHODS OF USING COMPOUNDS ACCORDING TO FORMULA I

Described herein are methods of using the novel compounds according to formula I, and the embodiments thereof, including fluorescent compounds according to formula I.

Compounds according to formula I are therapeutically useful. There are therefore provided uses of the compounds according to formula I in therapy and diagnostics, and therapeutic and diagnostic methods comprising administering a compound according to formula I, or a pharmaceutically acceptable salt thereof, to an individual.

Compounds according to formula I are effective as histone deacetylase inhibitors. Therefore, also provided is a method of inhibiting a histone deacetylase comprising contacting an effective amount of compound according to formula I, or a salt thereof, with a histone deacetylase. The method of inhibiting a histone deacetylase may be performed by contacting the histone deacetylase with a compound according to formula I, or a salt thereof, in vitro, thereby inhibiting histone deacetylase in vitro. The contacting may be performed in the presence of cells, wherein, optionally, the histone deacetylase is present within the cells, or alternatively may be performed in a cell free medium. Uses of such an in vitro method of inhibiting a histone deacetylase include, but are not limited to use in a screening assay (for example, wherein the compound according to formula I is used as a positive control or standard compared to compounds of unknown activity or potency in inhibiting histone deacetylase). The histone deacetylase may be any histone deacetylase, or a mixture of histone deacetylases. In some embodiments, the histone deacetylase is a class I deacetylase. In some embodiments, the histone deacetylase is a class II deacetylase. In some embodiments, the histone deacetylase is selected from HDAC1, HDAC2, HDAC3, HDAC6, and HDAC8.

The method of inhibiting a histone deacetylase may be performed by contacting the histone deacetylase with a compound according to formula I, or a salt thereof, in vivo, thereby inhibiting the histone deacetylase in vivo. The contacting is achieved by causing the compound according to formula I, or a salt thereof, to be present in the individual in an effective amount to achieve inhibition of the histone deacetylase. This may be achieved, for example, by administering an effective amount of the compound according to formula I, or a pharmaceutically acceptable salt thereof, to the individual, or by administering a prodrug of the compound according to formula I, or a pharmaceutically acceptable salt thereof. Uses of such an in vivo method of inhibiting a histone deacetylase include, but are not limited to use in methods of treating a disease or condition, wherein inhibiting histone deacetylase is beneficial, or treating or preventing diseases, wherein histone deacetylase activity contributes to the pathology and/or symptomology of the disease, as described in greater detail below.

Compounds according to formula I are effective to increase the amount of histone acetylation in a cell, particularly in the nucleus thereof. Therefore there is also provided a method of increasing the amount of histone acetylation in a cell comprising contacting the cell with an effective amount of compound according to formula I, or a salt thereof. The method may be performed by contacting the cell with a compound according to formula I, or a salt thereof, in vitro, thereby increasing the amount of histone acetylation in vitro. Uses of such an in vitro method of increasing the amount of histone acetylation include, but are not limited to use in a screening assay (for example, wherein the compound according to formula I is used as a positive control or standard compared to compounds of unknown activity or potency in increasing histone acetylation).

The method of increasing the amount of histone acetylation may also be performed by contacting the cell with a compound according to formula I, or a salt thereof, in vivo, thereby increasing the amount of histone acetylation in vivo. The contacting is achieved by causing the compound according to formula I, or a salt thereof, to be present in the individual in an effective amount to achieve an increase in the amount of histone acetylation. This may be achieved, for example, by administering an effective amount of the compound according to formula I, or a pharmaceutically acceptable salt thereof, to the individual, or by administering a prodrug of the compound according to formula I, or a pharmaceutically acceptable salt thereof. Uses of such an in vivo method of increasing the amount of histone acetylation include, but are not limited to use in methods of treating a disease or condition, wherein increasing the amount of histone acetylation is beneficial, or treating or preventing diseases, wherein histone deacetylation contributes to the pathology and/or symptomology of the disease, as described in greater detail below.

Compounds according to formula I are effective to increase the amount of tubulin acetylation and/or to inhibit tubulin deacetylation in a cell, particularly in the cytoplasm thereof. Therefore there is also provided a method of increasing the amount of tubulin acetylation in a cell comprising contacting the cell with an effective amount of compound according to formula I, or a salt thereof. Further, there is provided a method of inhibiting tubulin deacetylation in a cell comprising contacting the cell with an effective amount of compound according to formula I, or a salt thereof. The methods may be performed by contacting the cell with a compound according to formula I, or a salt thereof, in vitro, thereby increasing the amount of tubulin acetylation and/or inhibiting tubulin deacetylation in vitro. Uses of such an in vitro method of increasing the amount of tubulin acetylation and/or inhibiting tubulin deacetylation include, but are not limited to use in a screening assay (for example, wherein the compound according to formula I is used as a positive control or standard compared to compounds of unknown activity or potency in increasing the amount of tubulin acetylation and/or inhibiting tubulin deacetylation).

The methods of increasing the amount of tubulin acetylation and/or inhibiting tubulin deacetylation may also be performed by contacting the cell with a compound according to formula I, or a salt thereof, in vivo, thereby increasing the amount of tubulin acetylation and/or inhibiting tubulin deacetylation in vivo. The contacting is achieved by causing the compound according to formula I, or a salt thereof, to be present in the individual in an effective amount to achieve an increase the amount of tubulin acetylation and/or inhibition of tubulin deacetylation. This may be achieved, for example, by administering an effective amount of the compound according to formula I, or a pharmaceutically acceptable salt thereof, to the individual, or by administering a prodrug of the compound according to formula I, or a pharmaceutically acceptable salt thereof. Uses of such an in vivo method of increasing the amount of tubulin acetylation and/or inhibiting tubulin deacetylation include, but are not limited to use in methods of treating a disease or condition, wherein increasing the amount of tubulin acetylation and/or inhibiting tubulin deacetylation is beneficial, or treating or preventing diseases, wherein tubulin deacetylation contributes to the pathology and/or symptomology of the disease, as described in greater detail below.

The compounds according to formula I are effective to treat or prevent histone deacetylase-associated diseases and conditions. There is therefore provided a method of treating or prophylaxis of a histone deacetylase-associated disease or condition comprising causing an effective amount of a compound according to formula I, or a salt thereof, to be present in an individual in need of such treatment. This may be achieved, for example, by administering an effective amount of the compound according to formula I, or a pharmaceutically acceptable salt thereof, to the individual, or by administering a prodrug of the compound according to formula I, or a pharmaceutically acceptable salt thereof A "histone deacetylase-associated" disease or condition is a disease or condition, wherein a histone deacetylase possesses activity that contributes to the pathology and/or symptomology of the disease or condition or, wherein inhibition of a histone deacetylase produces an effect which is therapeutically beneficial. In some embodiments thereof, the disease or condition is a cancer. In some embodiments thereof, the compound according to formula I or salt thereof used is an embodiment of the compounds according formula I, or a salt thereof, as described above. In some embodiments, a fluorescent compound according to formula I is used.

The compounds according to formula I are effective to induce cell cycle arrest and/or apoptosis of a cell. There is therefore also provided a method of inducing cell-cycle arrest and/or apoptosis of a cell comprising contacting the cell with a compound according formula I, or a salt thereof. The method of inducing cell-cycle arrest and/or apoptosis of a cell may be performed by contacting the cell with a compound according to formula I, or a salt thereof, in vitro, thereby inducing cell-cycle arrest and/or apoptosis of a cell in vitro. Uses of such an in vitro method of inducing cell-cycle arrest and/or apoptosis include, but are not limited to use in a screening assay (for example, wherein the compound according to formula I is used as a positive control or standard compared to compounds of unknown activity or potency in inducing cell-cycle arrest and/or apoptosis). In some embodiments thereof, the cell-cycle arrest and/or apoptosis is induced in a cancer cell. In some embodiments thereof, the compound according to formula I or salt thereof used is an embodiment of the compounds according formula I, or a salt thereof, as described above. In some embodiments, the compound is a fluorescent compound according to formula I.

The method of inducing cell-cycle arrest and/or apoptosis of a cell may be performed by contacting the histone deacetylase with a compound according to formula I, in vivo, thereby inducing cell-cycle arrest and/or apoptosis in an individual in vivo. The contacting is achieved by causing the compound according to formula I, or a salt thereof, to be present in the individual in an amount effective to achieve inhibition of cell-cycle arrest and/or apoptosis. This may be achieved, for example, by administering an effective amount of the compound according to formula I, or a pharmaceutically acceptable salt thereof, to the individual, or by administering a prodrug of a compound according to formula I, or a pharmaceutically acceptable salt thereof. Uses of such an in vitro method of inducing cell-cycle arrest and/or apoptosis include, but are not limited to use in methods of treating a disease or condition, wherein inducing cell-cycle arrest and/or apoptosis is beneficial. In some embodiments thereof, the cell-cycle arrest and/or apoptosis is induced in a cancer cell, for example in a patient suffering from cancer. The method is preferably performed by administering an effective amount of the compound according to formula I, a prodrug of a compound according to formula I, or salt of either, to an individual who is suffering from cancer. In some embodiments thereof, the compound according to formula I or salt thereof used is an embodiment of the compounds according to formula I, or a salt thereof, as described above. In some embodiments, the compound is a fluorescent compound according to formula I.

The compounds according to formula I are also effective to treat cancer. There is therefore provided a method for treating cancer comprising causing an effective amount of a compound according to formula I, or a salt thereof, to be present in an individual, thereby increasing the amount of histone acetylation in vivo. The causing may be achieved by administering an effective amount of a compound according to formula I, or a salt thereof, to an individual in need of such treatment, or administering a prodrug of such a compound.

The compounds according to formula I are believed effective against a broad range of cancers and tumor types, including but not limited to bladder cancer, brain cancer, breast cancer, colorectal cancer, cervical cancer, gastrointestinal cancer, genitourinary cancer, head and neck cancer, lung cancer, ovarian cancer, prostate cancer, renal cancer, skin cancer, and testicular cancer. In some embodiments of the provided method of treating cancer, the compound according to formula I or salt thereof used is an embodiment of the compounds according to formula I, or a salt thereof, as described above.

More particularly, cancers that may be treated by the compounds, compositions and methods described herein include, but are not limited to, the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers, including, for example, hepatoma, e.g., hepatocellular carcinoma; cholangiocarcinoma; hepatoblastoma; angiosarcoma; hepatocellular adenoma; and hemangioma;

bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

nervous system cancers, including, for example, cancers of the skull, e.g., osteoma, hemangioma, granuloma, xanthoma, and osteitis defoinians; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non Hodgkin's lymphoma (malignant lymphoma) and Waldenstrom's macroglobulinemia;

skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma.

Cancers may be solid tumors that may or may not be metastatic. Cancers may also occur, as in leukemia, as a diffuse tissue. Thus, the term "tumor cell", as provided herein, includes a cell afflicted by any one of the above identified disorders.

The compounds according to formula I can also be administered in combination with existing methods of treating cancers, for example by chemotherapy, irradiation, or surgery. Thus, there is further provided a method of treating cancer comprising administering an effective amount of a compound according to formula I, or a salt thereof, to an individual in need of such treatment, wherein an effective amount of at least one further cancer chemotherapeutic agent is administered to the individual. Examples of suitable chemotherapeutic agents include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

Also provided is a method of treating cancer comprising administering an effective amount of a compound according to formula I, or a salt thereof, to an individual in need of such treatment, wherein an effective amount of ionizing radiation is administered to the individual. In these methods, the further cancer therapeutic agent and/or the ionizing radiation may be administered concomitantly and/or non-concomitantly with the compound according to formula I. Without being limited by theory, since the compounds according to formula I will sensitize the tumor cells to the effect of the second chemotherapeutic agent, particularly if the chemotherapeutic agent is one which damages DNA, or to the effect of the ionizing radiation, it may be advantageous for the administration of the compound according to formula I to precede the administration of the further chemotherapeutic agent or the ionizing radiation.

The compounds according to formula I can also be administered to an individual in combination with surgical methods to treat cancers, e.g., resection of tumors. The compounds can be administered to the individual prior to, during, or after the surgery. The compounds can be administered parenterally or injected into the tumor or surrounding area after tumor removal, e.g., to minimize metastases or to treat residual tumor cells present. In embodiments where the compound is fluorescent, the compound may be used to detect the presence of the tumor and to guide surgical resection. Such fluorescent compounds can further therapeutically treat the cancer through their histone deacetylase inhibitory properties. Accordingly, there is provided a method of guided surgery to remove at least a portion of a tumor from an individual comprising providing a fluorescent histone deacetylase inhibitor; causing the fluorescent histone deacetylase inhibitor to be present in at least some tumor cells in an effective amount to inhibit a histone deacetylase and for fluorescence to be observable; observing the fluorescence; and performing surgery on the individual to remove at least a portion of the tumor that comprises fluorescent tumor cells. Causing the fluorescent histone deacetylase inhibitor to be present can occur by administering a compound according to formula I, or a prodrug or salt thereof, to an individual.

In a further aspect there is provided a method of killing a tumor cell comprising contacting the tumor cell with an effective amount of a compound according to formula I, or a salt thereof; and contacting the tumor cell with an effective amount of at least one further chemotherapeutic agent.

In a further aspect there is provided a method of killing a tumor cell comprising contacting the tumor cell with an effective amount of a compound according to formula I, or a salt thereof; and irradiating the tumor cell with an effective amount of ionizing radiation.

In a further aspect there is provided a method of treating a tumor in an individual comprising causing an effective amount of a compound according to formula I, or a salt thereof, to be present in the individual; and irradiating the tumor with an effective amount of ionizing radiation.

Causing an effective amount of the compound according to formula I, or a salt thereof, may be achieved, for example, by administering an effective amount of the compound according to formula I, a prodrug of a compound according to formula I, or a pharmaceutically acceptable salt thereof, to the individual.

In the methods of treatment described herein, the compounds according to formula I may be administered to individuals (mammals, including animals and humans) afflicted with a disease such as such as cancer. In particular embodiments, the individual treated is a human.

The compounds may be administered by any route, including oral, rectal, sublingual, and parenteral administration. Parenteral administration includes, for example, intravenous, intramuscular, intraarterial, intraperitoneal, intranasal, intravaginal, intravesical (e.g., to the bladder), intradermal, transdermal, topical or subcutaneous administration. Also contemplated is the instillation of a drug in the body of the patient in a controlled formulation, with systemic or local release of the drug to occur at a later time. For example, the drug may be localized in a depot for controlled release to the circulation, or for release to a local site of tumor growth. Advantageously, the compounds are administered in the form of a pharmaceutical composition.

One or more compounds useful in the practice of the methods described herein may be administered simultaneously, by the same or different routes, or at different times during treatment. The compounds may be administered before, along with, or after other medications, including other compounds.

The treatment using methods of treatment described herein may be carried out for as long a period as necessary, either in a single, uninterrupted session, or in discrete sessions. The treating physician will know how to increase, decrease, or interrupt treatment based on patient response. According to one embodiment, treatment is carried out for from about four to about sixteen weeks. The treatment schedule may be repeated as required.

There is additionally provided a compound according to formula I, or any of the embodiments thereof, or a salt thereof, for use in any of the aforementioned methods of treatment or diagnosis, or for use in treatment or diagnosis of any of the aforementioned diseases or conditions. Also provided is a use of a compound according to formula I, or any of the embodiments thereof, or a salt thereof, for use in the manufacture of a medicament or diagnostic agent, for use in any of the aforementioned methods of treatment or diagnosis, or for use in treatment or diagnosis of any of the aforementioned diseases or conditions.

A method of trapping histone deacetylase in the cytoplasm of a cell is provided comprising contacting the cell with an effective amount of a compound according formula I, or any of the embodiments thereof, or a salt thereof, whereby the contacting results in an increase in the relative concentration of histone deacetylase in the cytoplasm of the cell as compared to the nucleus of the cell. In some embodiments, the histone deacetylase is a type II histone deacetylase. In some embodiments, the histone deacetylase is HDAC4. While not being limited by any theory, it is believed that the mechanism of action may involve inhibiting the transfer of histone deacetylase from the cytoplasm to the nucleus of the cell, or promoting the transfer of histone deacetylase from the nucleus to the cytoplasm of the cell.

Also provided is a method of detecting histone deacetylase inhibitory activity of a compound comprising contacting the compound with a cell; comparing the distribution of a histone deacetylase in the cell after contacting with the distribution of the histone deacetylase in the cell before contacting or the distribution of the histone deacetylase in a control cell which has not been contacted with the compound to determine whether the contacting with the compound results in an increase in the relative concentration of histone deacetylase in the cytoplasm of the cell as compared to the nucleus of the cell; and identifying a compound, the contacting of which results in an increase in the relative concentration of histone deacetylase in the cytoplasm of the cell as compared to the nucleus of the cell, as an inhibitor of histone deacetylase. In some embodiments, the histone deacetylase is a type II histone deacetylase. In some embodiments, the histone deacetylase is HDAC4.

X. METHODS OF USING FLUORESCENT HISTONE DEACETYLASE INHIBITORS, INCLUDING FLUORESCENT COMPOUNDS ACCORDING TO FORMULA I

Fluorescent compounds according to formula I provide added diagnostic and tracking functionalities to the therapeutic functionality of compounds according to formula I. Thus, in a further aspect, there are provided methods of using fluorescent histone deacetylase inhibitors, including fluorescent compounds according to formula I, and salts thereof.

One such method provided is a method of detecting the presence of an elevated amount of a histone deacetylase in a subject cell comprising providing a fluorescent histone deacetylase inhibitor; contacting the fluorescent histone deacetylase inhibitor with the subject cell and with a control cell; and observing fluorescence of the subject and control cells after the contacting; wherein an elevated level of fluorescence of the subject cell relative to the level of fluorescence of the control cell is indicative of an elevated amount of the histone deacetylase in the subject cell as compared to the control cell.

In an embodiment thereof, fluorescence of the cytoplasm of the cells is observed after the contacting, whereby an elevated amount of the histone deacetylase in the cytoplasm of the subject cell as compared to the control cell is detected. In certain embodiments, elevated amounts of acetylated histones in the nucleus can also be detected. In yet other embodiments, elevated amounts of acetylated tubulins in the cytoplasm can also be detected.

Uses of the provided method of detecting elevated histone deacetylase include, but are not limited to, detecting the presence of disease conditions associated with an elevated level of histone deacetylase activity and/or amount.

Accordingly, there is also provided a method of detecting diseased (e.g., cancerous) cells in an individual, comprising providing a fluorescent histone deacetylase inhibitor; contacting the fluorescent histone deacetylase inhibitor with a tissue of the individual; and observing for fluorescence of the cells of the tissue after the contacting; wherein an elevated level of fluorescence of at least some of the cells in the tissue relative to other cells in the tissue or relative to control non-diseased cells that have been contacted with the fluorescent histone deacetylase inhibitor is indicative that the fluorescent cells may be diseased cells comprising elevated amounts of a histone deacetylase.

In some embodiments thereof, the contacting is performed in vitro.

In other embodiments, the contacting is performed in vivo, for example by causing an effective amount of a fluorescent histone deacetylase inhibitor to be present in the tissue, e.g., by administering an effective amount of a fluorescent histone deacetylase inhibitor or a prodrug thereof to an individual.

In another aspect there is provided a method of radiotherapy of tumors comprising providing a fluorescent histone deacetylase inhibitor; causing the fluorescent histone deacetylase inhibitor to be present in the tumor cells in an effective amount to inhibit histone deacetylase and for fluorescence to be observable; observing the fluorescence; and directing an effective amount of ionizing radiation to the fluorescent tumor cells.

An advantage of the provided method of radiotherapy of tumors using fluorescent histone deacetylase inhibitors is that the fluorescent histone deacetylase inhibitor simultaneously renders the tumor cells visible and sensitized to the effect of the ionizing radiation. Since the tumor cells are visible, the irradiation can be directed to the tumor tissue, avoiding unnecessary damage to undiseased tissue. At the same time, the applied radiation is more effective since the tumor cells are sensitized to its effect. Further, by directing the radiation selectively to the tumor cells, the amount of radiation applied to the tumor tissue can, if desirable, be maximized since the radiation which is applied can be focused upon the tumor tissue made visible though its fluorescence.

In another aspect, there is provided a method of guided surgery or resection of at least a portion of a tumor, comprising providing a fluorescent histone deacetylase inhibitor, causing the fluorescent histone deacetylase inhibitor to be present in at least some cells of the tumor tissue in an effective amount for fluorescence of the tumor tissue to be observable, observing the fluorescence, and surgically removing at least some of the fluorescent tumor tissue, whereby at least a portion of the tumor that comprises fluorescent tumor cells is removed. Causing the fluorescent histone deacetylase inhibitor to be present can occur by administering a compound according to formula I, or a prodrug or salt thereof, to an individual. An advantage of the methods is that the fluorescent compounds simultaneously render the tumor cells visible while potentially also therapeutically treating the cancer through their histone deacetylase inhibitory properties. Since the tumor cells are visible, the surgery can be focused on the tumor tissue, avoiding unnecessary damage to undiseased tissue, while also minimizing the opportunity for some tumor to be inadvertently left behind.

In particular embodiments of each of the aforementioned methods of using fluorescent histone deacetylase inhibitors, the fluorescent histone deacetylase inhibitor is a compound according to formula I, or a salt thereof, or any of the embodiments thereof. Preferred are compounds according to formula I, wherein $Ar^1$ is monosubstituted 1-naphthyl, wherein the 5-position of the 1-naphthyl is substituted by —N(($C_1$-$C_6$) alkyl)$_2$ and wherein -L- is —(CH$_2$)$_n$—, wherein n is 4, 5, 6, 7 or 8. Particularly preferred is a compound selected from the group consisting of:
6-(5-(dimethylamino)naphthalene-1-sulfonamido)-N-hydroxypentanamide;
6-(5-(dimethylamino)naphthalene-1-sulfonamido)-N-hydroxyhexanamide;
6-(5-(dimethylamino)naphthalene-1-sulfonamido)-N-hydroxyheptanamide; and
6-(5-(dimethylamino)naphthalene-1-sulfonamido)-N-hydroxyoctanamide;
and salts of any thereof.

XI. METHODS OF PREDICTING THE SUSCEPTIBILITY OF CANCER TO TREATMENT WITH HISTONE DEACETYLASE INHIBITORS

In another aspect, there is provided a method for predicting the susceptibility of a cancer to treatment with histone deacetylase inhibitors comprising contacting a cancer cell with a histone deacetylase inhibitor, comparing the distribution of a histone deacetylase in the cell after contacting with the distribution of the histone deacetylase in the cell before contacting or the distribution of the histone deacetylase in a control cell which has not been contacted with the compound to determine whether the contacting with the compound results in an increase in the relative concentration of histone deacetylase in the cytoplasm of the cell as compared to the nucleus of the cell. The susceptibility of the cancer is determined to be increased when the contacting results in an increase in the relative concentration of the histone deacetylase in the cytoplasm of the cell as compared to the nucleus of the cell.

In some embodiments, the histone deacetylase is a type II histone deacetylase, for example HDAC4.

The provided methods may be used to predict whether the histone deacetylase inhibitor will be effective for treating cancer. In some embodiments, the method further include treating a patient with the cancer, by causing a compound, the contacting of which results in an increase in the relative concentration of histone deacetylase in the cytoplasm of the cancer cell as compared to the nucleus of the cancer cell, to be administered to the patient for the treatment of the cancer.

EXAMPLES

The following non-limiting examples are provided for illustrative purposes.
General Experimental Methods.
NMR spectra were recorded using a Varian-400 spectrometer for $^1$H (400 MHz) and $^{13}$C (100 MHz). Chemical shifts (δ) are given in ppm downfield from tetramethylsilane, an internal standard, and coupling constants (J-values) are in hertz (Hz). Purifications were performed by flash chromatography.

Examples 1-4

Exemplary Compounds of Formula I

The synthetic scheme for the synthesis of Examples 1-4 is shown in Scheme 5. The yields given in Scheme 5 are those for the synthesis of 6-(5-(dimethylamino)naphthalene-1-sulfonamido)-N-hydroxyhexanamide (i.e. n=2, Example 1).

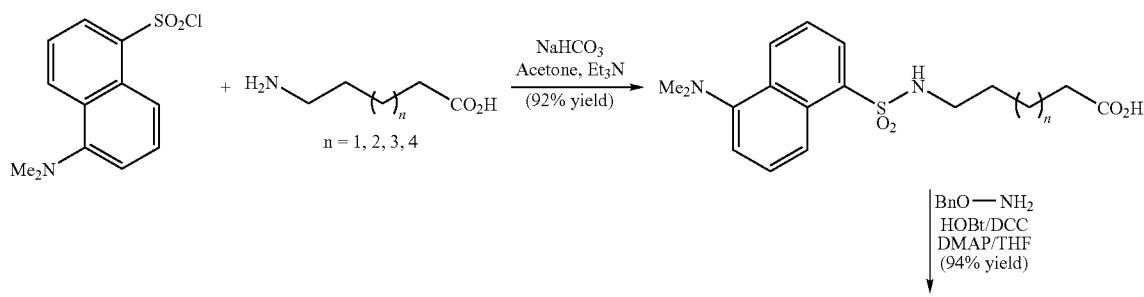

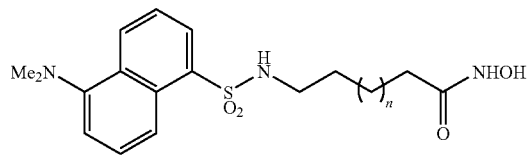

Example 1

6-(5-(Dimethylamino)naphthalene-1-sulfonamido)-N-hydroxyhexanamide

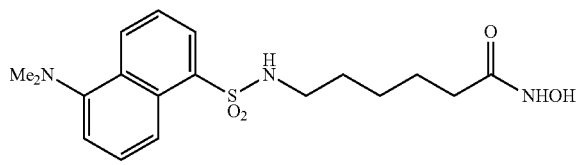

(a) 6-(5-Dimethylaminonaphthalene-1-sulfonamido) hexanoic acid 6 (n=2)

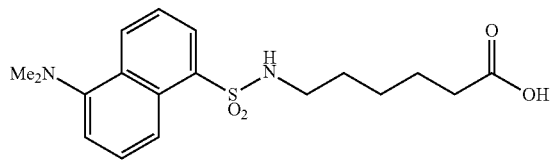

To a stirred solution of 6-aminohexanoic acid (1.5 g, 11.4 mmol) in 1 M NaHCO$_3$ (45 as added 5-(dimethylamino) naphthalene-1-sulfonyl chloride (0.63 g, 2.33 mmol) in acetone (10 mL) and triethylamine (2 mL). The solution was stirred for 1 h, acidified to pH 3 with 2 N HCl, extracted with ethyl acetate (3×15 mL). The organic layer was washed with water (15 mL) and brine (15 mL), dried over Na$_2$SO$_4$. The solvent was evaporated and purified by flash chromatography using CH$_2$Cl$_2$-MeOH to afford 6-(5-dimethylaminonaphthalene-1-sulfonamido)hexanoic acid as a green sticky oil (0.76 g, 92%). $^1$H NMR (CDCl$_3$, 400 MHz) δ 10.66 (br, 1H), 8.46 (d, 1H, J=8.4 Hz), 8.33 (d, 1H, J=8.4 Hz), 8.19 (d, 1H, J=7.2 Hz), 7.44 (m, 2H), 7.09 (d, 1H, J=7.6 Hz), 5.66 (br, 1H), 2.85 (m, 2H), 2.79 (s, 6H), 2.08 (t, 2H, J=8.8, 7.6 Hz), 1.32 (m, 4H), 1.12 (m, 2H); $^{13}$C NMR (100 MHz) δ 179.29, 151.67, 135.03, 130.18, 129.72, 129.58, 129.25, 128.26, 123.16, 119.01, 115.20, 45.30, 42.88, 33.98, 29.07, 25.74, 24.01.

(b) N-(Benzyloxy)-5-(5-(dimethylamino)naphthalene-1-sulfonamido)hexanamide

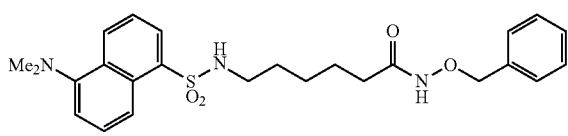

To an ice bath cooled solution of 6-(5-dimethylaminonaphthalene-1-sulfonamido)hexanoic acid (0.53 g, 1.45 mmol) in THF (25 mL) was added 1-hydroxybenzotriazole (HOBt, 0.24 g, 1.75 mmol), 4-dimethylamino pyridine (DMAP, 0.21 g, 1.75 mmol), and dicyclohexylcarbodiimide (DCC, 0.40 g, 1.93 mmol), followed by O-benzylhydroxylamine (0.22 g, 1.75 mmol). The mixture was stirred at room temperature for 48 h. Water (15 mL) was added to the mixture and stirred at room temperature for 10 minutes. The precipitate was filtered off, and the filtrate was extracted with ethyl acetate (3×15 mL). The organic layer was washed with water and brine, dried over Na$_2$SO$_4$. The solvent was evaporated and the residue was purified by flash chromatography using CH$_2$Cl$_2$-MeOH to afford N-(benzyloxy)-5-(5-(dimethylamino)naphthalene-1-sulfonamido)hexanamide as green sticky oil (0.64 g, 94%). $^1$H NMR (CDCl$_3$, 400 MHz) δ 9.04 (br, 1H), 8.47 (d, 1H, J=8.4 Hz), 8.29 (d, 1H, J=8.4 Hz), 8.17 (dd, 1H, J=0.8, 1.2 Hz), 7.47 (m, 2H), 7.27 (m, 5H), 7.12 (d, 1H, J=7.6 Hz), 5.40 (br, 1H), 4.81 (s 2H), 2.82 (s, 6H), 2.79 (m, 2H), 1.83 (m, 2H), 1.33 (m, 4H), 1.09 (m, 2H); $^{13}$C NMR (100 MHz) δ 170.90, 157.35, 151.96, 135.02, 130.39, 129.93, 129.72, 129.50, 129.22, 128.64, 128.56, 128.45, 123.31, 119.00, 115.31, 78.13, 45.49, 43.02, 33.92, 29.13, 25.69, 25.04.

(c) 6-(5-(Dimethylamino)naphthalene-1-sulfonamido)-N-hydroxyhexanamide

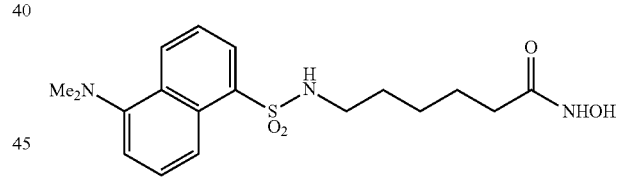

To a solution of N-(benzyloxy)-5-(5-(dimethylamino) naphthalene-1-sulfonamido)hexanamide (0.50 g, 1.06 mmol) in methanol (20 mL) was added 10% palladium on carbon (113.0 mg, 0.106 mmol), the apparatus was degassed and then filled with hydrogen under atmosphere pressure. The reaction was allowed to stir at room temperature until starting material disappeared completely by TLC(CH$_2$Cl$_2$/MeOH: 10:1, R$_f$=0.5). The suspension was then filtered through a pad of celite and concentrated under reduced pressure, the residue was purified by flash chromatography using CH$_2$Cl$_2$-MeOH to afford the title compound as yellow soft solid (0.38 g, 94%). $^1$H NMR (CDCl$_3$, 400 MHz) δ 9.65 (br, 1H), 8.47 (d, 1H, J=8.4 Hz), 8.30 (d, 1H, J=4.4 Hz), 8.17 (d, 1H, J=6.0 Hz), 7.44 (m, 2H), 7.10 (d, 1H, J=6.8 Hz), 5.85 (br, 1H), 2.83 (s, 8H), 2.04 (m, 2H), 1.38 (m, 4H), 1.18 (m, 2H); $^{13}$C NMR (100 MHz) δ 172.05, 151.92, 135.14, 130.39, 129.96, 129.79, 129.44, 128.54, 123.40, 119.23, 115.42, 45.57, 43.04, 32.60, 29.10, 25.70, 24.76; LC-MS: m/z 380 (MH$^+$); HRMS: 380.1648 (MH$^+$).

Example 2

6-(5-(dimethylamino)naphthalene-1-sulfonamido)-N-hydroxypentanamide

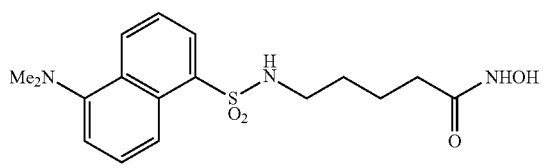

Prepared in 97% overall yield by a route analogous to that described in Example 1 starting from 5-aminopentanoic acid and obtained as a soft yellow solid. $^1$H NMR (CDCl$_3$, 400 MHz) δ 9.84 (br, 1H), 8.46 (d, 1H, J=8.4 Hz), 8.23 (m, 2H), 7.43 (m, 2H), 7.08 (m, 1H, J=6.8 Hz), 6.13 (br, 1H), 2.83 (m, 8H), 2.11 (m, 2H), 1.52 (m, 4H); $^{13}$C NMR (100 MHz) δ 172.08, 151.67, 135.01, 130.16, 129.77, 129.62, 129.17, 128.41, 123.32, 119.18, 115.31, 45.45, 42.78, 32.24, 28.91, 22.47; LC-MS: m/z 366 (MH$^+$); HRMS: 366.1471 (MH$^+$).

Example 3

6-(5-(dimethylamino)naphthalene-1-sulfonamido)-N-hydroxyheptanamide

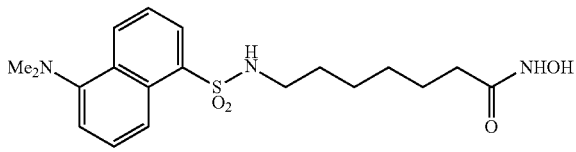

Prepared in 90% overall yield by a route analogous to that described in Example 1 starting from 5-aminoheptanoic acid and obtained as a soft yellow solid. $^1$H NMR (CDCl$_3$, 400 MHz) δ 9.72 (br, 1H), 8.47 (d, 1H, J=7.2 Hz), 8.25 (m, 2H), 7.45 (m, 2H), 7.11 (m, 1H), 5.78 (br, 1H), 2.82 (m, 8H), 2.02 (m, 2H), 1.27 (m, 8H); $^{13}$C NMR (100 MHz) δ 171.94, 151.68, 135.06, 130.15, 129.71, 129.58, 129.17, 128.31, 123.23, 119.05, 115.20, 45.37, 43.06, 32.52, 29.19, 28.13, 25.73, 25.08; HRMS: 394.1746 (MH$^+$).

Example 4

6-(5-(dimethylamino)naphthalene-1-sulfonamido)-N-hydroxyoctanamide

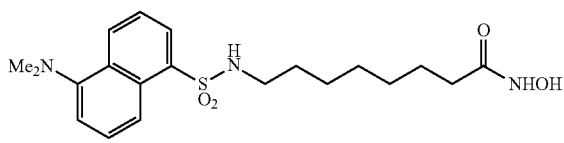

Prepared in 33% overall yield by a route analogous to that described in Example 1 starting from 5-aminooctanoic acid=and obtained as a yellow soft solid. $^1$H NMR (CDCl$_3$, 400 MHz) δ 8.47 (d, 1H, J=7.2 Hz), 8.25 (m, 2H), 7.46 (m, 2H), 7.11 (m, 1H), 5.76 (br, 1H), 2.82 (m, 8H), 2.10 (m, 2H), 1.34 (m, 4H), 1.04 (m, 6H); $^{13}$C NMR (100 MHz) δ 171.16, 151.92, 135.17, 130.42, 129.95, 129.81, 129.50, 128.57, 123.45, 119.23, 115.42, 45.63, 43.33, 32.97, 29.50, 28.71, 28.50, 26.15, 25.36; HPLC: Method A, retention time=3.26 min; Method B, retention time=4.53 min; LC-MS: m/z 408 (MH$^+$); HRMS: 408.1954 (MH$^+$).

Physical Properties

A summary of the physical properties of the compounds of Examples 1 to 4 is given in Table 1.

TABLE 1

Physical Properties of Example Compounds.

| Example | n | MW | clogP | MV ($^3$) | Emiss (nm) | Exc (nm) |
|---|---|---|---|---|---|---|
| 2 | 1 | 365.45 | 1.19 | 1037.4 | | |
| 1 | 2 | 379.48 | 1.72 | 1067.5 | 500 | 320 |
| 3 | 3 | 393.50 | 2.25 | 1104.2 | | |
| 4 | 4 | 407.53 | 2.78 | 1194.5 | | |

Legend: MW = molecular weight; PSA = polar surface area; clogP = calculated log of the octanol/water partition coefficient; MV = molecular volume; Emiss = emission wavelength; Exc = excitation wavelength

Molecular Modeling

In order to design a potent histone deacetylase inhibitor, homology models to represent each histone deacetylase isoform were developed. Initially, the structure of HDAC7 was used to predict the structure of HDAC6. From the sequence and structural comparison of various histone deacetylase isoforms, it appeared that each histone deacetylase isoform was unique in its CAP region. This CAP region interacts with the surface of the protein, a region nearer to the catalytic core. This unique recognition motif might be used to differentiate the histone deacetylase isoforms and develop isoform selective inhibitors. Unexplored regions denoted as subsites (S1, S2, S3) that are located on the surface of the protein, and one in the vicinity of the zinc site were identified. The S1 subsite is surrounded by the hydrophobic residues such as Y306, F208, and tryptophan. Analysis showed that residues in this region differ among histone deacetylase isoforms, thus it was concluded that bulky groups such as fused bicyclic aromatic groups, particularly if appropriately substituted, targeting this area could favorably increase selectivity and potency. Advantageously, it was predicted that this could be an area of the histone deacetylase enzyme that would tolerate a large fluorescent probe. This critical structural analysis provided a basis the design of the compounds of formula I. While not being limited by theory, it was hypothesized that compounds that interact with the surface regions (S1, S2 and S3) may provided for enhanced potency and, potentially, isoform selectivity towards histone deacetylases.

The structures of the compounds of Examples 1-4 were docked into the models of the various histone deacetylase isoforms. As an example, using this rigid type of protein docking simulation, a root mean standard deviation (RMSD) of ~3.1 Å for the docking of the compound of Example 1 with HDAC8 was found. This relatively poor RMSD was due mainly to the different positioning of the CAP group. Another potential contributor to the poor result could be that the scoring functions may not be suitable for zinc metal binding ligands. In order to avoid the caveat of poor scoring functions and to include protein flexibility in the calculations, molecular dynamics (MD) simulations were performed on HDAC8 using all of the initial binding modes previously found. In these docking simulations, the zinc atom was included with zinc parameters computed from quantum mechanical simulations.

The results of such a molecular dynamic simulation is illustrated in FIG. 1, which shows the results of molecular modeling of the compound of Example 1 (6-(5-(Dimethylamino)naphthalene-1-sulfonamido)-N-hydroxyhexanamide) and suberoylanilide hydroxamic acid into a model based on the HDAC-8 X-ray structure with a molecular dynamic simulation of 50 ps. Potentially important molecular interactions are indicated with circles and arrows.

The compounds of Examples 1-4 were selected as potentially particularly advantageous compounds and hence as preferred embodiments of the compounds according to formula I using this analysis.

Biological Properties

1. Pan-HDAC Inhibition Activities

The values of $IC_{50}$ concentrations of HDAC inhibitors were determined using a fluorimetric histone deacetylase assay kit supplied by Biomol following the manufacturer's instructions. The kits use the Fluor de Lys (Fluorimetric Histone deAcetylase Lysyl) Substrate and Developer combination and provides an assay that can be carried out in two simple mixing steps, all on the same 96-well plate. First, the Fluor de Lys Substrate which comprises an acetylated lysine side chain, is incubated with a sample containing histone deacetylase activity. Deacetylation of the substrate sensitizes the substrate so that, in the second step, mixing with the Fluor de Lys Developer generates a fluorophore.

For the pan-HDAC assay, HeLa nuclear extracts were used as a source of histone deacetylase and were prepared in 0.1 M KCl, 20 mM Hepes/NaOH at pH 7.9, 20% glycerol, 0.2 mM DTA, 0.5 mM DTT, and 0.5 mM PMSF. The HDAC assay was performed using Fluor de Lys substrate and concentrations (nM to μM) of compounds at 37° C. in HDAC assay buffer, containing 25 mM Tris/Cl, pH 8.0, 137 mM NaCl, 2.7 mM KCl, 1 mM $MgCl_2$. Reactions were stopped after 15 min with Fluor de Lys Developer. Fluorescence was measured with an excitation at a wave-length of 360 nm and emitted light of 460 nm (TECAN ULTRA 384) was detected. Negative (no enzyme, no inhibitor, a drug with no HDAC inhibition activity) and positive controls (a HeLa nuclear extract with no HDAC inhibitor and known HDAC inhibitors; TSA and SAHA) were included in the assay reactions. The reaction was performed in triplicate for each sample. Each point represents the mean±SD of replicates.

The potency of the compounds of Examples 1 to 4 in a Pan-HDAC inhibition assay is summarized in Table 2. The data showed that compounds with both five carbon and six carbon spacer were particularly effective pan-HDAC inhibitors. This was surprising given that the known histone deacetylase inhibitors (i.e. compounds like suberoylanilide hydroxamic acid (SAHA)) have a six carbon linker.

TABLE 2

Pan-HDAC Inhibition Activities of Example Compounds.

| Example | n | HDAC $IC_{50}$ (nM) |
|---|---|---|
| 2 | 1 | 286.6 |
| 1 | 2 | 125 |
| 3 | 3 | 116.3 |
| 4 | 4 | 208 |

Legend: HDAC $IC_{50}$ = Inhibitory potency in a pan-HDAC inhibition assay

2. HDAC Isoform Inhibition Activities

The histone deacetylase isoform inhibition assays were performed using the Biomol Fluor-de-Lys histone deacetylase assay kit as described above for the pan-HDAC assay, except that instead of HeLa nuclear extracts, purified histone deacetylase proteins of the various isoforms was used.

The potency of the compounds of Examples 1 and 3 and suberoylanilide hydroxamic acid (SAHA) in inhibiting the histone deacetylase isoforms HDAC1, HDAC2, HDAC3, HDAC6 and HDAC8 was examined. The results are summarized and compared with the pan-HDAC inhibition potency in Table 3.

TABLE 3

Histone Deacetylase Isoform Inhibition Activities.

| Compound | n | pan-HDAC $IC_{50}$ (nM) | HDAC Isoform $IC_{50}$ (nM) | | | | |
|---|---|---|---|---|---|---|---|
| | | | HDAC1 | HDAC2 | HDAC3 | HDAC6 | HDAC8 |
| Example 1 | 2 | 125 | 955.8 | 1376 | 1120 | 128.9 | 2898 |
| Example 3 | 3 | 116 | 1292 | 7398 | 4886 | 76.2 | 2311 |
| SAHA | — | 80 | 220.7 | 557.6 | 1787 | 27.0 | 1698 |

Legend: HDAC $IC_{50}$ = Inhibitory potency in a pan-HDAC or HDAC isoform inhibition assay 3. Cell Growth Inhibition Activities The effect of the compound of Example 1 in inhibiting the growth of various cell lines is summarized in Table 4. The cell lines used were PC-3 (prostate cancer), C42 (androgen-independent prostate cancer), LNCap (androgen-dependent prostate cancer), SQ20B (squamous cell carcinoma), MCF7 (breast cancer) and MDA-231 (breast cancer).

Cells were seeded at 5,000 per well in 80 ml of growing medium in 96-well tissue culture plates. At 24 hours after seeding, a solution of the compound or DMSO vehicle control were added to each well to a total volume of 100 ml (three replicates per concentration), and incubated for 48 hours at 37° C. Growth inhibition was determined using CellTiter 96® $AQ_{ueous}$ One Solution Cell Proliferation according to manufacturer's instructions (*Technical Bulletin: CellTiter 96® AQueous One Solution Cell Proliferation Assay. Instructions* for Use of Products G3580, G3581 and G3582; Promega, Inc. Madison, Wis., Revised 4/2005), and the absorbance measured at 490 nm on a microplate reader. The CellTiter 96® AQ$_{ueous}$ One Solution Cell Proliferation Assay is a colorimetric method for determining the number of viable cells in proliferation, cytotoxicity or chemosensitivity assays and contains a tetrazolium compound [3-(4,5-dimethylthiazol-2-yl)-5-(3-carboxymethoxyphenyl)-2-(4-sulfophenyl)-2H-tetrazolium, inner salt; "MTS"] and an electron coupling reagent (phenazine ethosulfate; PES). The MTS tetrazolium compound (Owen's reagent) is bioreduced by cells into a colored formazan product that is soluble in tissue culture medium. Assays are performed by adding a small amount of the CellTiter 96® AQueous One Solution Reagent directly to culture wells, incubating for 1-4 hours and then recording the absorbance at 490 nm with a 96-well plate reader. The quantity of formazan product as measured by the absorbance at 490 nm is directly proportional to the number of living cells in culture.

The 50% growth inhibition (IG$_{50}$) was calculated as the compound concentration required to reduce cell number by 50% compared with control. Results are summarized in Table 4.

TABLE 4

Cell Growth Inhibition Activities.

[Chemical structure: Me$_2$N-naphthalene-SO$_2$-NH-(CH$_2$)$_n$-C(O)-NHOH]

| Compound | n | PC3 | C42 | LNCap | SQ20B | MCF7 | MDA-231 |
|---|---|---|---|---|---|---|---|
| Example 1 | 2 | 1.538 | 1.913 | 1.224 | 6.425 | 9.199 | 12.2 |

Legend: Proliferation IG$_{50}$ = Inhibitory potency in a cell growth assay versus the various cell lines 4. Effect of Compounds on Cell Cycle Distribution The effect of the compound of Example 1 was compared to the effect of suberoylanilide hydroxamic acid (SAHA) in affecting the cell cycle distribution of various cell lines was evaluated. The cell cycle distribution of various cell lines both in the absence of compound and 24 hours after adding the compound of Example 1 or suberoylanilide hydroxamic acid (SAHA) was measured.

LNCap and PC-3 cells were incubated in the presence or absence of compound. The cells were harvested at the indicated time points after addition of compound then washed twice with cold phosphate-buffered saline. Cells (1-2×10$^6$) were resuspended in 0.5 ml of ice-cold phosphate-buffered saline, and single cell suspension was verified microscopically. The cell suspension was gradually mixed with ice-cold absolute ethanol to the final volume of 2.0 ml, and cooled on ice at least for 20 min before staining with propidium iodide. The cell cycle distributions were measured in a fluorescence-activated cell sorter from Becton Dickinson. DNA content was quantified using ModFit LT 3.0 software (Verity Software House, Inc.).

The compound of Example 1 shifts the cell cycle distribution to increase the percentage of cells in G1 as compared to S or G2 in a comparable fashion to the known effective anti-cancer histone deacetylase inhibitor suberoylanilide hydroxamic acid.

TABLE 5

Effect of Compounds on Cell Cycle Distributions.

[Chemical structure: Me$_2$N-naphthalene-SO$_2$-NH-(CH$_2$)$_n$-C(O)-NHOH]

| Cell Line | Compound | n | G1 | S | G2 |
|---|---|---|---|---|---|
| PC-3 | None | — | 47.29 | 21.15 | 31.56 |
| PC-3 | SAHA | — | 72.28 | 14.33 | 13.39 |
| PC-3 | Example 1 | 2 | 64.35 | 19.91 | 15.74 |
| LNCap | None | — | 72.50 | 18.95 | 8.55 |
| LNCap | Example 1 | 2 | 85.23 | 9.18 | 5.59 |

Legend: Cell cycle distribution in the absence of compound or 24 after adding the compound of Example 1 or suberoylanilide hydroxamic acid (SAHA)

6. Imaging Demonstrating that the Fluorescent Histone Deacetylase Inhibitor of Example 1 ((6-(5-(dimethylamino) naphthalene-1-sulfonamido)-N-hydroxyhexanamide)) Localizes in the Cytoplasm of Cells Measurement of the emission and excitation spectra for the compound of Example 1 was performed to confirm the corresponding range for fluorescent visualization in cancer cells and to confirm the fluorescent property of the compound.

Human prostate cancer cell lines PC-3 and DU145 cells were plated down onto glass slides at a density of 500,000 per slide and incubated overnight. The original medium (RPMI w/10% FBS, 1% pen/strep and 1% L-Glu) was removed and replaced by medium containing 20 μM of the compound of Example 1 and incubated for one hour. The slides were then washed three times with phosphate-buffered saline. The cells were then fixed with a 4% solution of formaldehyde for ten minutes, washed four times with phosphate-buffered saline and mounted. For slides with nuclear staining, cells were treated with propidium iodide (1:1000) for 4 minutes after fixation, washed four times with PBS and mounted.

The compound of Example 1 at 20 μM was imaged using a multiphoton laser with an excitation wavelength of 700 nm and an emission wavelength of 510 nm. Propidium Iodide was imaged with an excitation wavelength of 535 and an emission wavelength of 617. Images were taken at 63×.

Figure 2:
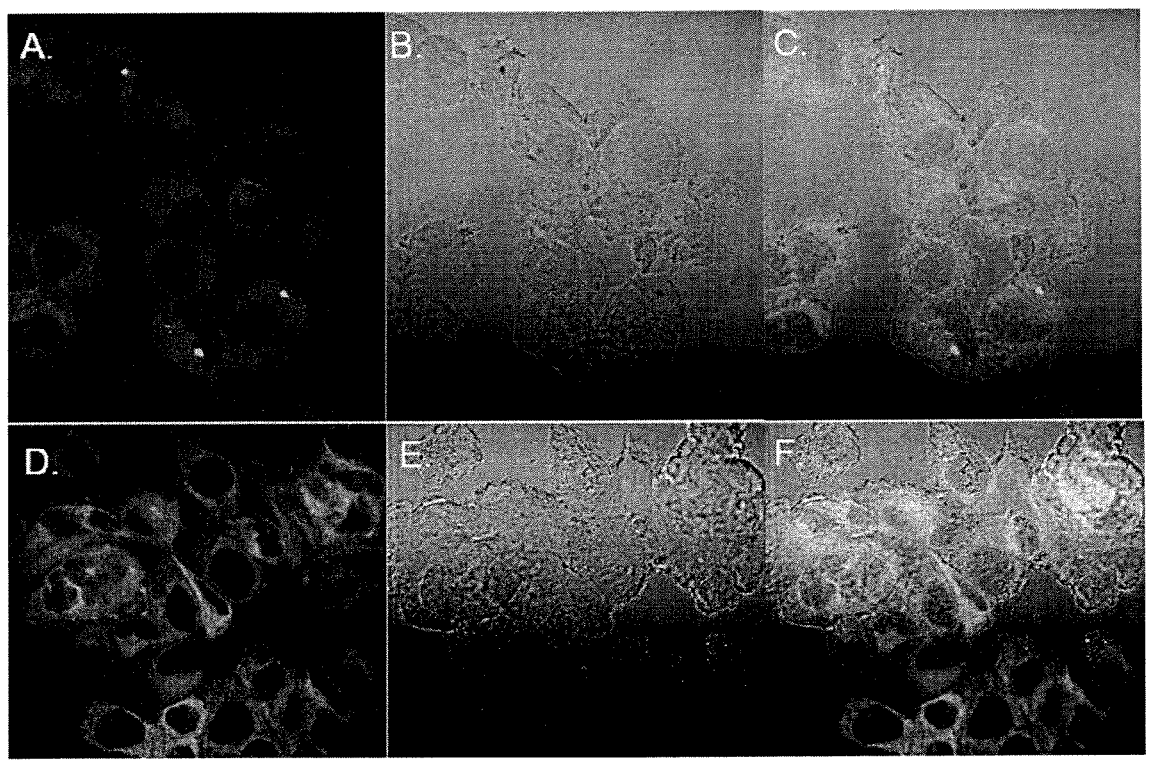
FIG. 2 shows imaging demonstrating that the fluorescent histone deacetylase inhibitor of Example 1 ((6-(5-(dimethylamino)naphthalene-1-sulfonamido)-N-hydroxyhexanamide)) is present in the cytoplasm but not the nucleus of cells. Images A-C show the effect of treating PC-3 cells with (6-(5-(dimethylamino)naphthalene-1-sulfonamido)-N-hydroxyhexanamide) (20 µM) for 60 minutes. In image A the compound is seen fluorescing (green fluorescence) in the cytoplasm. Image B is a bright field image. Image C is a merger of A and B. Images D-F show the effect of treating DU-145 cells with (6-(5-(dimethylamino)naphthalene-1-sulfonamido)-N-hydroxyhexanamide) (20 µM) for 60 minutes. Image D the compound is seen fluorescing (green fluorescence) in the cytoplasm. Image E is a bright field image. Image F is a merger of D and E.

The results of the experiment are shown in FIG. 2, which shows imaging demonstrating that the fluorescent histone deacetylase inhibitor of Example 1 ((6-(5-(dimethylamino) naphthalene-1-sulfonamido)-N-hydroxyhexanamide)) is present in the cytoplasm but not the nucleus of cells. Images A-C show the effect of treating PC-3 cells with (6-(5-(dimethylamino)naphthalene-1-sulfonamido)-N-hydroxyhexanamide) (20 μM) for 60 minutes. Image A the compound is seen fluorescing (green fluorescence) in the cytoplasm. Image B is a bright field image. Image C is a merger of A and B. Images D-F show the effect of treating DU-145 cells with 6-(5-(dimethylamino)naphthalene-1-sulfonamido)-N-hydroxyhexanamide (2004) for 60 minutes. Image D the compound is seen fluorescing (green fluorescence) in the cytoplasm. Image E is a bright field image. Image F is a merger of D and E.

Figure 3:
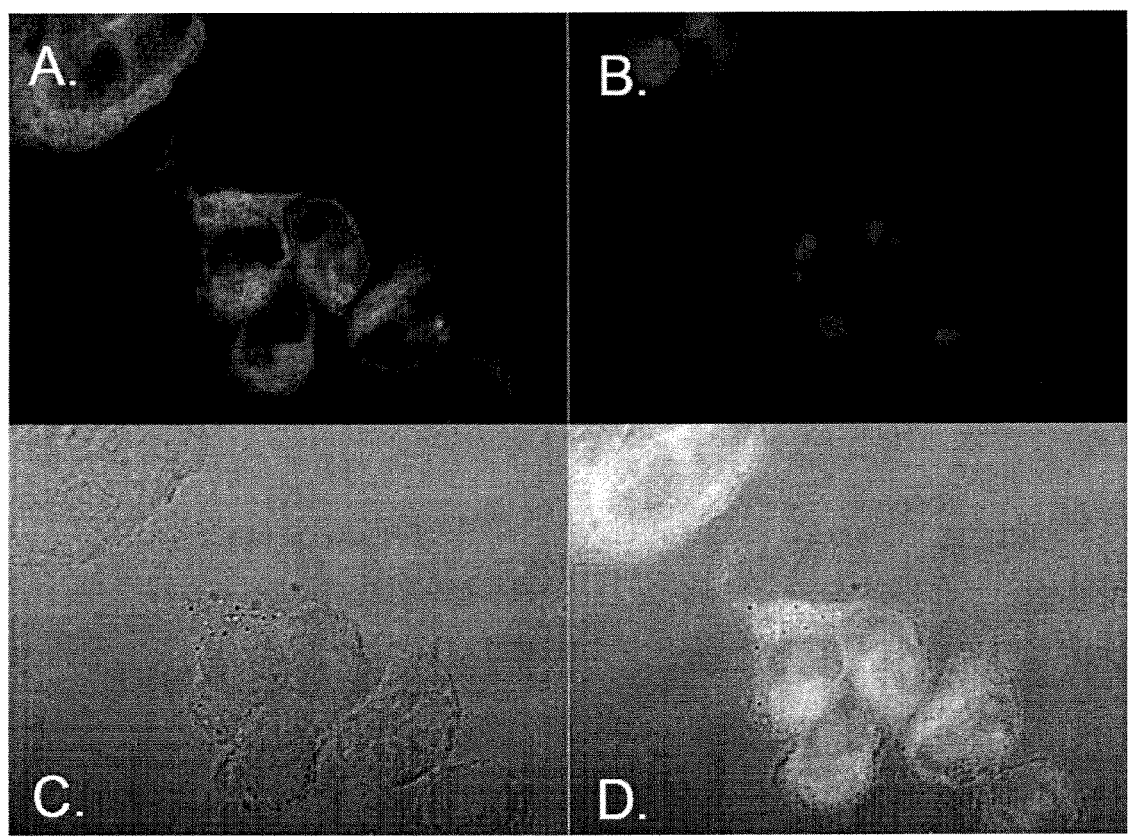
FIG. 3 shows imaging demonstrating that the fluorescent histone deacetylase inhibitor of Example 1 ((6-(5-(dimethylamino)naphthalene-1-sulfonamido)-N-hydroxyhexanamide)) does not localize to nuclei that are stained with propidium iodide. PC3 cells are shown after 60 min. exposure to 20 µM concentration of the compound. Image A shows the fluorescent histone deacetylase inhibitor (green fluorescence). Image B shows nuclei stained with propidium iodide (red). Image C is a DIC image. Image D overlays images A B and C and shows the histone deacetylase inhibitor (green) fluorescence in the cytoplasm, away from the propidium iodide (red) fluorescence of the nuclei.

Co-localization experiments also reveal that 6-(5-(dimethylamino)naphthalene-1-sulfonamido)-N-hydroxyhexanamide does not localize to nuclei that are stained with propidium iodide (FIG. 3). In FIG. 3, images recorded using a multiphoton laser at 695 nM show PC3 cells after 60 min. exposure to 20 μM concentration of the compound. Image A shows the fluorescent histone deacetylase inhibitor (green fluorescence). Image B shows nuclei stained with propidium iodide (red). Image C is a DIC image. Image D overlays images A B and C and shows the histone deacetylase inhibitor (green) fluorescence in the cytoplasm, away from the propidium iodide (red) fluorescence of the nuclei.

Figure 4:
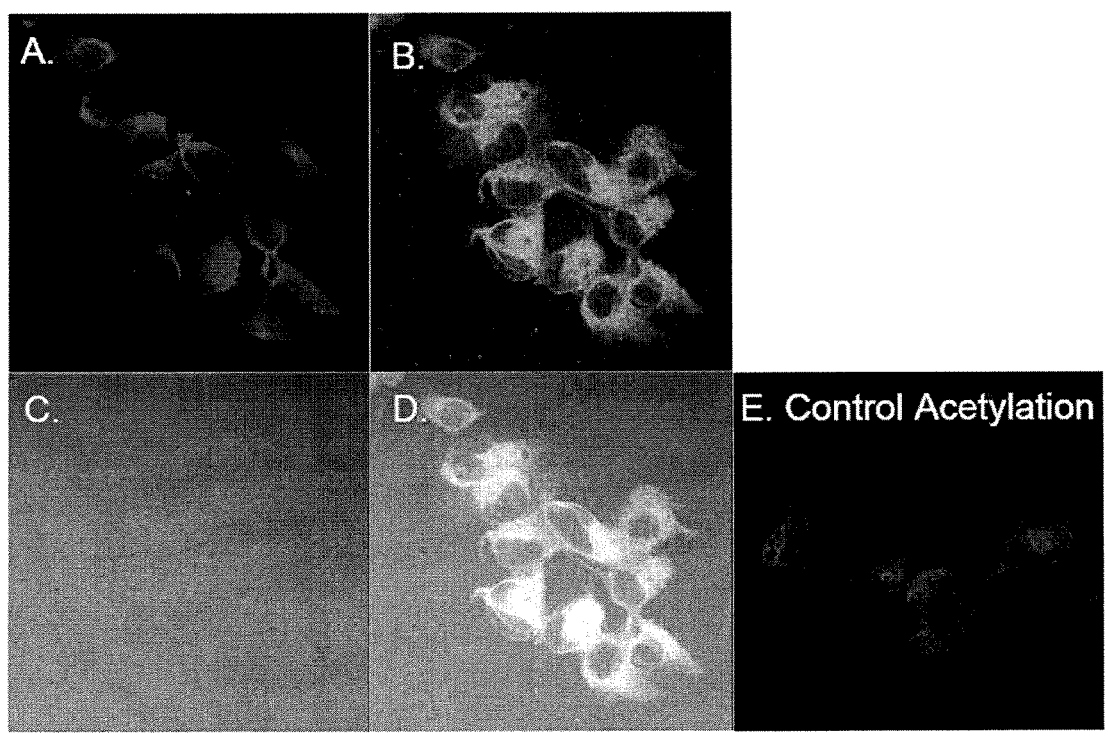
FIG. 4 shows imaging demonstrating that the fluorescent histone deacetylase inhibitor of Example 1 ((6-(5-(dimethylamino)naphthalene-1-sulfonamido)-N-hydroxyhexanamide)) causes increased tubulin acetylation in the cytoplasm of A549 cells. Images A, B, and C show the cells after treatment with the histone deacetylase inhibitor (20 µM) for 60 minutes. FIG. A shows acetylated tubulin (red fluorescence). Image B shows the histone deacetylase inhibitor fluorescence (green). Image C is the DIC image, while image D is a merger of images A, B, and C. Image E shows a control level of acetylated tubulin (obtained without treatment with the histone deacetylase inhibitor).

7. Imaging Demonstrating that the Fluorescent Histone Deacetylase Inhibitor of Example ((6-(5-(dimethylamino)naphthalene-1-sulfonamido)-N-hydroxyhexanamide)) Increases Tubulin and Histone Acetylation (a) Inhibitory Effects on Tubulin Deacetylation The results of an experiment showing the effect of the fluorescent histone deacetylase inhibitor of Example 1 ((6-(5-(dimethylamino)naphthalene-1-sulfonamido)-N-hydroxyhexanamide)) in increasing tubulin acetylation in the cytoplasm of A549 (lung cancer) cells is shown in FIG. 4. Images A, B, and C show the cells after treatment with the histone deacetylase inhibitor (20 μM) for 60 minutes. FIG. A shows acetylated tubulin (red fluorescence). Image B shows the histone deacetylase inhibitor fluorescence (green). Image C is the DIC image, while image D is a merger of images A, B, and C. Image E shows a control level of acetylated tubulin (obtained without treatment with the histone deacetylase inhibitor). The increased tubulin acetylation is evidenced by the higher level of tubulin fluorescence in Image A as compared to the control Image E. As with other cell lines, the histone deacetylase inhibitor fluoresces in the cytoplasm of the cells.

(b) Inhibitory Effects on Histone Deacetylation

Figure 5:
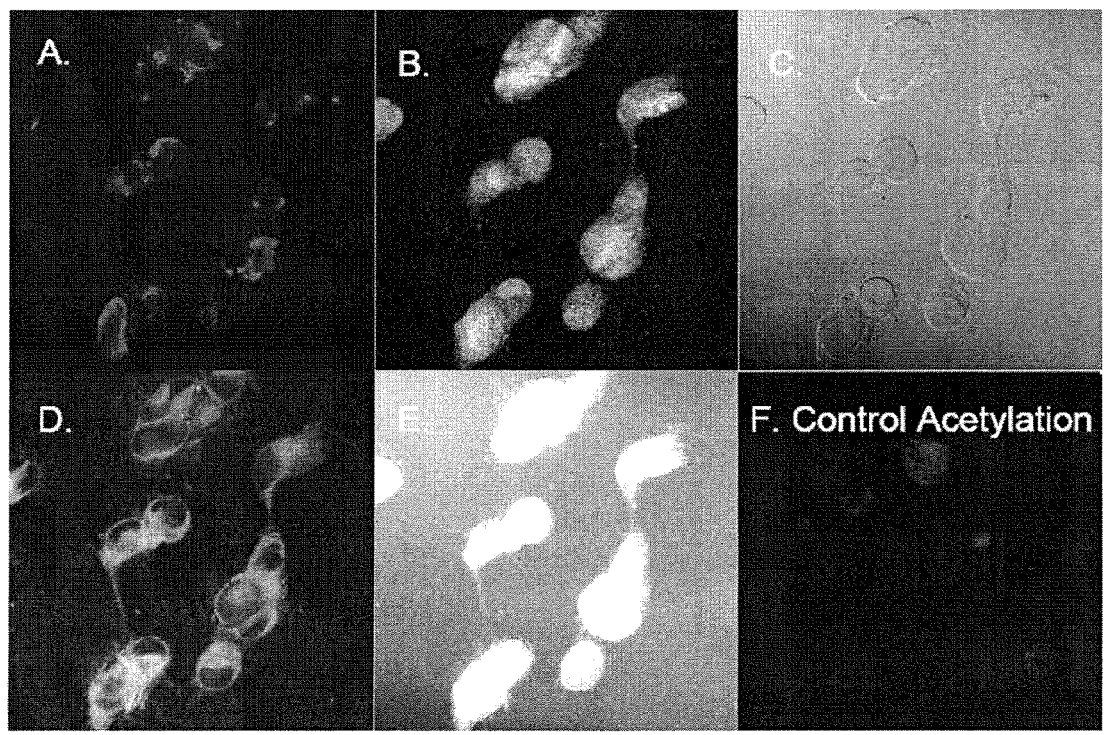
FIG. 5 shows imaging demonstrating that the fluorescent histone deacetylase inhibitor of Example 1 ((6-(5-(dimethylamino)naphthalene-1-sulfonamido)-N-hydroxyhexanamide)) causes increased histone acetylation in the nucleus of A549 cells. Images A, B, C and D show the cells after treatment with the histone deacetylase inhibitor (20 µM) for 60 minutes. FIG. A shows acetylated histone (red fluorescence). Image B shows a propidium iodide stain of the nucleus. Image C is the DIC image. Image 4 shows the histone deacetylase inhibitor fluorescence (green) while image E is a merger of images A, B, C, and D. Image F shows a control level of acetylated histone (obtained without treatment with the histone deacetylase inhibitor).

The results of an experiment showing the effect of the fluorescent histone deacetylase inhibitor of Example 1 ((6-(5-(dimethylamino)naphthalene-1-sulfonamido)-N-hydroxyhexanamide)) in increasing histone acetylation in the nucleus of A549 cells is shown in FIG. 5. Images A, B, C and D show the cells after treatment with the histone deacetylase inhibitor (20 μM) for 60 minutes. FIG. A shows acetylated histone (red fluorescence). Image B shows a propidium iodide stain of the nucleus. Image C is the DIC image. Image 4 shows the histone deacetylase inhibitor fluorescence (green) while image E is a merger of images A, B, C, and D. Image F shows a control level of acetylated histone (obtained without treatment with the histone deacetylase inhibitor). The increased nuclear histone acetylation is evidenced by the higher level of tubulin fluorescence in Image A as compared to the control Image F. Surprisingly histone deacetylase inhibitor causes increased nuclear acetylation even though the compound itself is localized in the cytoplasm of the cells and not in the nucleus, as indicated by the compound fluorescence.

8. Imaging Demonstrating that the Histone Deacetylase Inhibitor of Example 14645-(Dimethylamino)naphthalene-1-sulfonamido)-N-hydroxyhexanamide)) and Suberoylanilide Hydroxamic Acid Trap Histone Deacetylase in the Cytoplasm of Cells Human prostate cancer PC3 cells were cultured in Dulbecco's Modified Eagle's Medium (DMEM) with 5% serum at 37° C. over night. Test compounds (the compound of Example 1 or suberoylanilide hydroxamic acid (SAHA)) were added to different tissue culture dishes to the final concentration of 1 μM and incubated with the cells. Control cells were incubated in the absence of test compound.

After 24 hours, the cells were washed with phosphate-buffered saline (1×) one time, and fixed with 4% percent of paraformaldehyde for 15 min. Non specific binding was blocked with 10% normal goat serum in phosphate-buffered saline containing 0.2% tween-20 (sigma aldrich P7949) for 1 hour. Cells were treated with mouse monoclonal anti-HDAC4 antibody (Sigma Aldrich H0163) 1:200 dilution in 5% goat serum in PBS for 1 hour at room temperature. The cells were washed three times with phosphate buffered saline (1×). Fluorescently tagged rabbit anti-mouse monoclonal antibodies (Alexa fluor 488 from Invitrogen A11001) were applied to the cells for 30 minutes. The cells were washed with phosphate-buffered saline (1×) three times. Vecta shield mounting medium for florescence with DIPA (Vector laboratory H-1200) were loaded on the cells and covered with cover glass. The cells were then treated with HDAC4 antibody to visualize HDAC4 and with 4',6-diamidino-2-phenylindole (DAPI) to visualize the nuclei.

Fluorescence microscopy was used to observe the immunohistostaining results. Images were recorded at 695 nm using a multiphoton laser.

Figure 6:
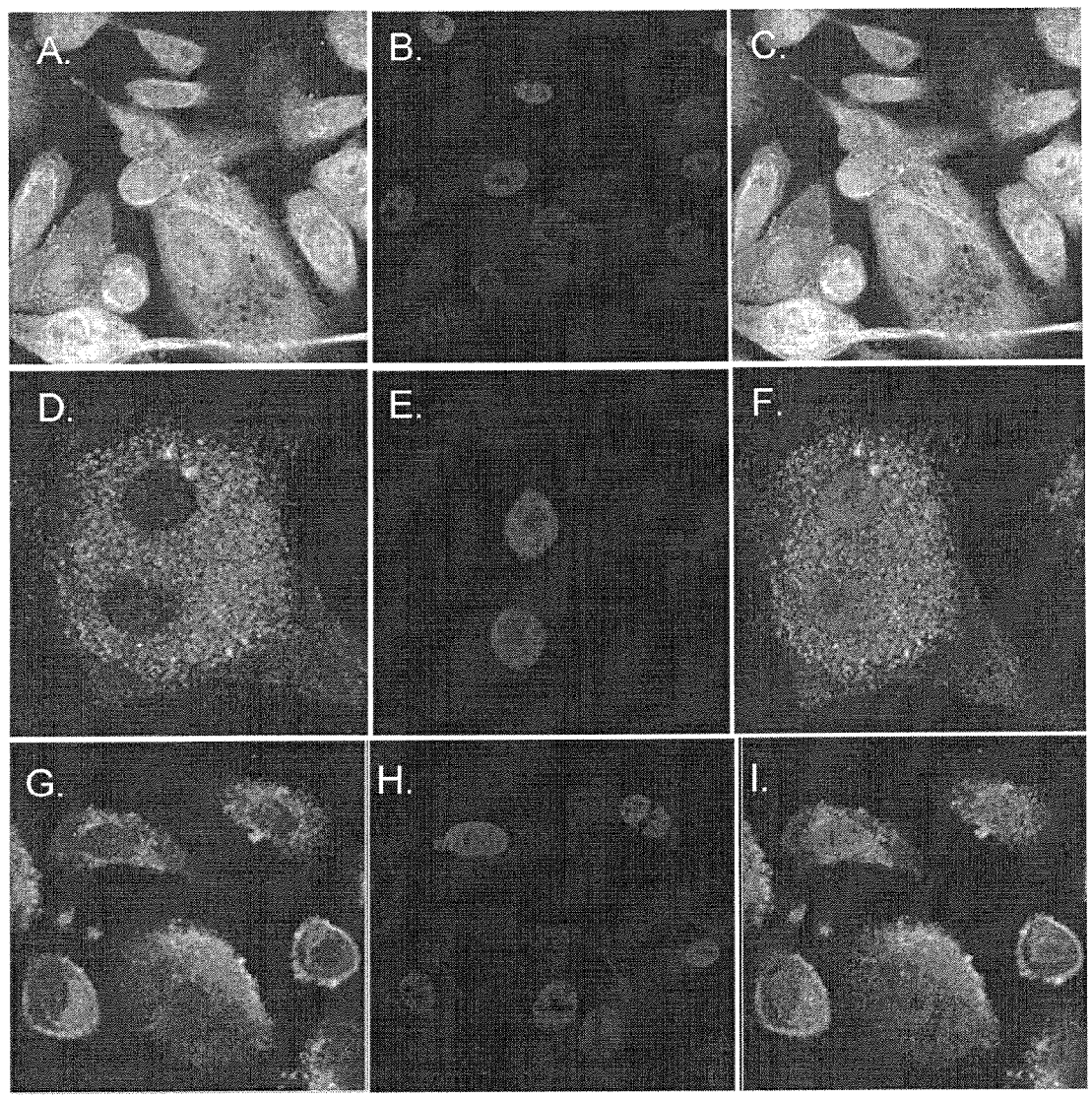
FIG. 6 shows imaging demonstrating that the histone deacetylase inhibitor of Example 1 ((6-(5-(dimethylamino) naphthalene-1-sulfonamido)-N-hydroxyhexanamide)) causes trapping of histone deacetylase in the cytoplasm of prostate cancer PC3 cells. Images A, D, and G shows the distribution of HDAC4 cells (green fluorescence), B, E, and J show nuclear staining with 4',6-diamidino-2-phenylindole (DAPI) (blue fluorescence). FIGS. C, F, and I show overlaps of A and B, D and E, and G and H respectively. Images A, B, and C are of untreated PC3 cells, images D, E, and F are images taken following treatment with ((6-(5-(dimethylamino)naphthalene-1-sulfonamido)-N-hydroxyhexanamide)) causes and G, H, and I are images taken following treatment with suberoylanilide hydroxamic acid (SAHA).

The results of the experiment are shown in FIG. 6 and show that both the histone deacetylase inhibitors tested trap HDAC4 in the cytoplasm of human prostate cancer cells. A. Image A shows PC3 cells which are untreated with a histone deacetylase inhibitor stained for HDAC4 (green fluorescence). Image B shows the nuclei of the untreated PC3 cells stained using 4',6-diamidino-2-phenylindole (DAPI). Comparison of images A and B (overlaid in image C) shows that the HDAC4 is present in both the cytoplasm and nucleus of the untreated cells.

Images D-F of FIG. 6 show the effect of the histone acetylase inhibitor of Example 1 ((6-(5-(dimethylamino)naphthalene-1-sulfonamido)-N-hydroxyhexanamide)) on HDAC4 distribution. Image D shows PC3 cells which have been treated with 1 μM ((6-(5-(dimethylamino)naphthalene-1-sulfonamido)-N-hydroxyhexanamide)) and stained for HDAC4 (green fluorescence). Image E shows the nuclei of the same cells stained using 4',6-diamidino-2-phenylindole (DAPI). Comparison of images D and E (overlaid in image F) shows that the compound treatment traps HDAC4 in the cytoplasm of the cells, with a much lower concentration of HDAC4 seen in the nuclei.

Images G-I of show a similar effect of suberoylanilide hydroxamic acid (SAHA) on HDAC4 distribution. Image G shows PC3 cells which have been treated with 1 μM suberoylanilide hydroxamic acid (SAHA) and stained for HDAC4 (green fluorescence). Image H shows the nuclei of the same cells stained using 4',6-diamidino-2-phenylindole (DAPI). Comparison of images G and H (overlaid in image F) shows that the compound treatment traps HDAC4 in the cytoplasm of the cells, with a much lower concentration of HDAC4 seen in the nuclei.

All references cited herein are incorporated by reference. A number of embodiments of the invention have been described. Nevertheless, it will be understood that various modifications may be made without departing from the spirit and scope of the invention. Accordingly, other embodiments are within the scope of the following claims.

What is claimed is:

1. A compound according to formula I:

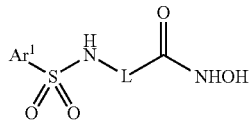

or a salt thereof;
wherein:
-L- is —(CH$_2$)$_n$—, wherein n is 4, 5, 6, 7 or 8; and
Ar$^1$ is a substituted 1-naphthyl, wherein the 5-position of the 1-naphthyl is substituted by a substituent selected from the group consisting of —OH, —O(C$_1$-C$_6$)alkyl, —NH$_2$, —N(CH$_3$)$_2$, —NH(C$_1$-C$_6$)alkyl, and —N((C$_1$-C$_6$)alkyl)$_2$.

2. A compound according to claim 1, or a salt thereof, wherein the 5-position of the 1-naphthyl is substituted by —N((C$_1$-C$_6$)alkyl)$_2$.

3. A compound according to claim 1, or a salt thereof, wherein the compound is: 6-(5-(dimethylamino)naphthalene-1-sulfonamido)-N-hydroxypentanamide, or a salt thereof.

4. A compound according to claim 1, or a salt thereof, wherein the compound is: 6-(5-(dimethylamino)naphthalene-1-sulfonamido)-N-hydroxyhexanamide, or a salt thereof.

5. A compound according to claim 1, or a salt thereof, wherein the compound is: 6-(5-(dimethylamino)naphthalene-1-sulfonamido)-N-hydroxyheptanamide, or a salt thereof.

6. A compound according to claim 1, or a salt thereof, wherein the compound is: 6-(5-(dimethylamino)naphthalene-1-sulfonamido)-N-hydroxyoctanamide, or a salt thereof.

7. A pharmaceutical composition comprising a pharmaceutically acceptable carrier and a compound according to claim 1, or a pharmaceutically acceptable salt thereof.

8. A pharmaceutical composition according to claim 7, or a pharmaceutically acceptable salt thereof, wherein the compound is selected from the group consisting of:
6-(5-(dimethylamino)naphthalene-1-sulfonamido)-N-hydroxypentanamide;
6-(5-(dimethylamino)naphthalene-1-sulfonamido)-N-hydroxyhexanamide;
6-(5-(dimethylamino)naphthalene-1-sulfonamido)-N-hydroxyheptanamide; and
6-(5-(dimethylamino)naphthalene-1-sulfonamido)-N-hydroxyoctanamide;
and pharmaceutically acceptable salts of any thereof.

9. A method of inhibiting a histone deacetylase comprising contacting an effective amount of compound according to claim 1, or a salt thereof, with a histone deacetylase.

10. A method according to claim 9, wherein the contacting is achieved by administering an effective amount of the compound, or a salt thereof, to an individual.

11. A method according to claim 9, wherein the histone deacetylase is a class II histone deacetylase.

12. A method according to claim 11, wherein the histone deacetylase is HDAC6.

13. A method of treating a histone deacetylase-associated disease or condition comprising administering an effective amount of a compound according to claim 1, or a salt thereof, to an individual.

14. A method according to claim 13, wherein the disease or condition is a cancer.

15. A method according to claim 13, wherein the compound is selected from the group consisting of:
6-(5-(dimethylamino)naphthalene-1-sulfonamido)-N-hydroxypentanamide;
6-(5-(dimethylamino)naphthalene-1-sulfonamido)-N-hydroxyhexanamide;
6-(5-(dimethylamino)naphthalene-1-sulfonamido)-N-hydroxyheptanamide; and
6-(5-(dimethylamino)naphthalene-1-sulfonamido)-N-hydroxyoctanamide;
and pharmaceutically acceptable salts of any thereof.

16. A method according to claim 14, wherein the cancer is selected from the group consisting of bladder cancer, brain cancer, breast cancer, colorectal cancer, cervical cancer, gastrointestinal cancer, genitourinary cancer, head and neck cancer, lung cancer, ovarian cancer, prostate cancer, renal cancer, skin cancer, and testicular cancer.

17. A method according to claim 14, further comprising administering an effective amount of at least one further cancer chemotherapeutic agent.

18. A method according to claim 14, further comprising administering an effective amount of ionizing radiation.

19. A method of killing a tumor cell comprising:
contacting the tumor cell with an effective amount of a compound according to claim 1, or a salt thereof; and
irradiating the tumor cell with an effective amount of ionizing radiation.

20. A method of killing a tumor cell comprising:
contacting the tumor cell with an effective amount of a compound according to claim 1, or a salt thereof; and
contacting the tumor cell with an effective amount of at least one further chemotherapeutic agent.

21. A method of killing a tumor cell, comprising providing to the tumor cell a histone deacetylase inhibitor and directing an effective amount of ionizing radiation to the tumor cell wherein the histone deacetylase inhibitor is a compound according to formula I:

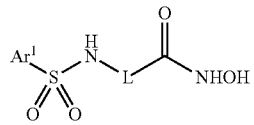

or a salt thereof;
wherein:
-L- is —(CH$_2$)$_n$—, wherein n is 4, 5, 6, 7 or 8; and
Ar$^1$ is a substituted 1-naphthyl, wherein the 5-position of the 1-naphthyl is substituted by a substituent selected from the group consisting of —OH, —O(C$_1$-C$_6$)alkyl, —NH$_2$, —N(CH$_3$)$_2$, —NH(C$_1$-C$_6$)alkyl, and —N((C$_1$-C$_6$)alkyl)$_2$.

* * * * *

UNITED STATES PATENT AND TRADEMARK OFFICE
CERTIFICATE OF CORRECTION

PATENT NO. : 8,293,513 B2
APPLICATION NO. : 12/747365
DATED : October 23, 2012
INVENTOR(S) : Milton L. Brown et al.

Page 1 of 1

It is certified that error appears in the above-identified patent and that said Letters Patent is hereby corrected as shown below:

In the Specification

In Column 1, Lines 11-17, delete "STATEMENT AS TO FEDERALLY SPONSORED RESEARCH Certain aspects of the disclosure provided herein were funded, in whole or in part, by the National Institute of Health P01 Grant # CA07417501. The Government has certain rights in the invention." and insert -- STATEMENT REGARDING FEDERALLY FUNDED RESEARCH
This invention was made with government support under grant number CA074175 awarded by the National Institutes of Health. The government has certain rights in the invention. --.

Signed and Sealed this
Second Day of January, 2024

Katherine Kelly Vidal
*Director of the United States Patent and Trademark Office*